US008461364B2

(12) United States Patent
Wheeler et al.

(10) Patent No.: US 8,461,364 B2
(45) Date of Patent: Jun. 11, 2013

(54) POLYMORPHS OF (S)-3-AMINOMETHYL-7-(3-HYDROXY-PROPOXY)-3H-BENZO[C][1,2] OXABOROL-1-OL

(75) Inventors: Conrad Wheeler, San Francisco, CA (US); Dan Todd, Collegeville, PA (US); Pingyun Chen, Collegeville, PA (US); Beth A. Norton, Collegeville, PA (US)

(73) Assignees: GlaxoSmithKline LLC, Philadelphia, PA (US); Anacor Pharmaceuticals, Inc., Palo Alto, CA (US)

( * ) Notice: Subject to any disclaimer, the term of this patent is extended or adjusted under 35 U.S.C. 154(b) by 168 days.

(21) Appl. No.: 12/641,318

(22) Filed: Dec. 17, 2009

(65) Prior Publication Data

US 2011/0152217 A1 Jun. 23, 2011

Related U.S. Application Data

(60) Provisional application No. 61/138,490, filed on Dec. 17, 2008.

(51) Int. Cl.
*C07F 5/02* (2006.01)
*A61K 31/69* (2006.01)

(52) U.S. Cl.
USPC ............................................... 556/7; 514/64

(58) Field of Classification Search
USPC ................................................ 556/7; 514/64
See application file for complete search history.

(56) References Cited

U.S. PATENT DOCUMENTS

| | | | |
|---|---|---|---|
| 2,260,336 A | 10/1941 | Prescott et al. |
| 3,873,279 A | 3/1975 | Singer |
| 4,602,011 A | 7/1986 | West et al. |
| 4,716,035 A | 12/1987 | Sampathkamar |
| 4,766,113 A | 8/1988 | West et al. |
| 4,894,220 A | 1/1990 | Nabi et al. |
| 5,348,947 A | 9/1994 | Patel et al. |
| 5,348,948 A | 9/1994 | Patel et al. |
| 5,591,731 A | 1/1997 | Kennedy et al. |
| 5,668,258 A | 9/1997 | Stolowitz |
| 5,688,928 A | 11/1997 | Stolowitz |
| 5,831,045 A | 11/1998 | Stolowitz et al. |
| 5,880,188 A | 3/1999 | Austin et al. |
| 5,962,498 A | 10/1999 | Driedger et al. |
| 6,083,903 A | 7/2000 | Adams et al. |
| 6,306,628 B1 | 10/2001 | Rothschild et al. |
| 6,369,098 B1 | 4/2002 | Pershadsingh et al. |
| 6,800,645 B1 | 10/2004 | Cox et al. |
| 6,855,848 B2 | 2/2005 | Scherer et al. |
| 7,169,603 B2 | 1/2007 | Hedley et al. |
| 7,217,701 B2 | 5/2007 | Mikoshiba et al. |
| 7,390,806 B2 | 6/2008 | Lee et al. |
| 7,465,836 B2 | 12/2008 | Lee et al. |
| 7,582,621 B2 | 9/2009 | Baker et al. |
| 7,767,657 B2 | 8/2010 | Baker et al. |
| 7,816,344 B2 | 10/2010 | Baker et al. |
| 2002/0028831 A1 | 3/2002 | Manley |
| 2002/0161230 A1 | 10/2002 | Meudt et al. |
| 2003/0032673 A1 | 2/2003 | Nagy |
| 2004/0224923 A1 | 11/2004 | Lee et al. |
| 2005/0054644 A1 | 3/2005 | Lee et al. |
| 2005/0125852 A1 | 6/2005 | Caenepeel et al. |
| 2006/0009386 A1 | 1/2006 | Stossel et al. |
| 2006/0222671 A1 | 10/2006 | Weidner |
| 2006/0234981 A1 | 10/2006 | Baker et al. |
| 2007/0155699 A1 | 7/2007 | Baker et al. |
| 2007/0286822 A1 | 12/2007 | Sanders et al. |
| 2007/0293457 A1 | 12/2007 | Baker et al. |
| 2009/0227541 A1 | 9/2009 | Baker et al. |
| 2010/0256092 A1 | 10/2010 | Xia et al. |

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |
| WO | WO 9533754 | 5/1995 |
| WO | WO 9812206 A1 | 3/1998 |
| WO | WO 0044387 A1 | 8/2000 |
| WO | WO 0075142 A2 | 12/2000 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005013892 A3 | 2/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009014309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Austin, et al., "Oxaboroles and Salts and their Use of Biocides for Plastics", CAS, vol. 124, pp. 234-024, (1996).
Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Progress on New Therapeutics for Fungal Nail Infections", Annual Reports in Medicinal Chemistry, vol. 40: pp. 323-335, (2005).
Bessis, N., "Gene Therapy for Rheumatoid Arthritis," J. Gene Med, vol. 4; pp. 581-591 (2002).

(Continued)

*Primary Examiner* — Bernard Dentz
(74) *Attorney, Agent, or Firm* — Barbara J. Carter

(57) ABSTRACT

This invention provides, among other things, polymorphs of the hydrochloride salt of (S)-3-aminomethyl-7-(3-hydroxy-propoxy)-3H-benzo[c][1,2]oxaborol-1-ol.

14 Claims, 25 Drawing Sheets

OTHER PUBLICATIONS

Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).

Cairns, et al., "Derivatives of 1,4-Xylene-2,5-diboronic acid and 1,4-xylene-2-boronic acid", J. Org. Chem. vol. 29; pp. 2810-2812, (1964).

Chander, et al. "Prevalence of Fungal Corneal Ulcers in Northern India", Infections, vol. 22, No. 3; pp. 207-209, (1994).

Chemical Abstracts Registry No. 845302-09-2, Entered STN Mar. 11, 2005.

Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).

Dale, et al., "Substituted Styrenes VIII Syntheses and some Reactions of the Vinylbenzeneboronic Acids" J. Org. Chem. vol. 27; pp. 2598-2603, (1962).

Denis, "Pharmacology 1104 Lecture: Drug Classifications & Characteristics of Antimicrobials" (2003).

Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).

Ferrer, Targeting Aminocytl-tRNA Synthetases for the Treatment of Fungal Infections, Drug News Perspective, vol. 19, No. 6; pp. 347-348, (Jul./Aug. 2006).

Fungicide: Definition from Answer.com, (1998).

Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).

Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).

Haynes, et al., "Arylboronic Acids VIII. Reactions of boronphthalide" J. Org. Chem. vol. 29, No. 11; pp. 3229-3233, (1964).

Hauck, et al., "Preparation and Anticonvulsant Activity of Some Arydialkkylsuccinimides" Research Lab of Parke Davis Co. (1967).

He, et al., "Small-Molecule Inhibition of TNF-alpha", Science, vol. 310, No. 5750; pp. 1022-1025, (Nov. 11, 2005).

Lampe, et al., "Synthesis and Protien Kinase Inhibitory Activity of Balanol Analogues with Modified Benzophenone Subunits", J. Med. Chem., vol. 45; pp. 2624-2643, (2002).

Lennarz, et al., "Arylboronic Acids. IV. Reactions of Boronophthalide" J. Am. Chem. Soc. vol. 82; pp. 2172-2175, (1960).

Li, et al., "An Improved Protocol for Preparation of 3-Pyridyl- and Some Arylboronic Acids", J. Org. Chem., vol. 67; pp. 5394-5397, (2002).

Koster, et al., "Cyclisierugen von Bor-Stickstoff-Verbindugen in der Hietz" Liebigs Ann. Chem., vol. 720; pp. 23-31, (1968).

Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).

McMillin, et al., "Systemic Aspects of Psoriasis: An Intergrative Model Based on Intestinal Etiology", Int. Med. vol. 2, Issue 2/3, (1999).

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).

Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).

Mudran, "Drug Delivery to the Nail Following Topical Application", International Journal of Pharmaceutics, vol. 236: pp. 1-26, (2002).

Patani, et al., "Bioterrorism: A Rational Approach to Drug Design", Chem. Rev., vol. 96; pp. 3147-3176 (1996).

Qin, et al., "Luminescent Organoboron Quinolate Polymers," Journal of the American Chemical Society, vol. 126, No. 22; pp. 7015-7018, (Jun. 9, 2004).

Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).

Snyder, et al. "Common Bacteria Whose Susceptibility to Antimicrobials in no longer Predictable" J. Med. Liban, vol. 48 No. 4; pp. 208-214, (2000).

Sugar, et al., "Comparison of Three Methods of Antifungal Susceptibility Testing with the Proposed NCCLS Stardard Broth Macrodilution Assay: Lack of Effect of Phenol Red" Diagn. Microbiol. Infect. Dis. vol. 21; pp. 129-133, (1995).

Tabuchi, et al., "Anticoccidial Activity of some Azacyclo Organoborinates," Heterocycles, vol. 60, No. 01; pp. 177-182, (2003).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).

Tschampel, et al., "Arylboronic Acids. VII. Some Reactions to o-Formybenzeneboronic Acids", J. Org. Chem. vol. 29, No. 8; pp. 2168-2172, (1964).

Turner, et al., Current Pharmaceutical Design, vol. 2; pp. 209-224 (1996).

Vippagunta, "Crystalline Solids", Advanced Drug Delivery Reviews, vol. 48; pp. 3-26, (2001).

Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).

Ye, et al., "Convenient and Versatile Synthesis of formyl-substituted Benzoxaboroles", Tetrahedron, vol. 65; pp. 8738-8744, (2009).

Zhdankin, et al., "Synthesis and Structure of Benzoboroxoles: Novel Organboron Heterocycles," Tetrahedron Letters, vol. 40; pp. 6705-6708, (1999).

Zhou, et al., "Hemodextrin: a Self-assembled Cyclodextrin-Porphyrin Construct That Binds Dioxygen," Biophysical Chemistry, 105:639-648 (2003).

Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).

Zhou, et al., "Pattern Recognition of Proteins Based on an Array of Functionalized Porphyrins," J. Am. Chem. Soc., 128:2421-2425 (2006).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

Caira, Crystalline Polymorphism of Organic Compounds, Topics in Current Chemistry 198: 163-208 (1998).

Figure 1B

| Angle (2θ) | 6.2 | 8.8 | 9.8 | 12.4 | 13.9 | 17.7 | 22.3 | 23.1 | 24.3 | 24.8 | 26.1 | 27.2 | 28.0 | 30.9 | 32.2 | 33.2 |

Figure 2B

| Angle (2θ) | 14.1 | 20.2 | 21.1 | 26.6 |

Figure 3B

| Angle (2θ) | 7.8 | 12.3 | 14.0 | 20.2 | 21.3 | 22.4 | 23.3 | 24.7 | 27.6 | 32.1 |

Figure 4B

| Angle (2θ) | 12.1 | 12.8 | 14.2 | 15.5 | 17.7 | 18.2 | 19.2 | 20.2 | 21.1 | 22.0 | 22.8 | 24.4 | 26.6 | 27.7 | 31.6 | 32.5 |
|---|---|---|---|---|---|---|---|---|---|---|---|---|---|---|---|---|

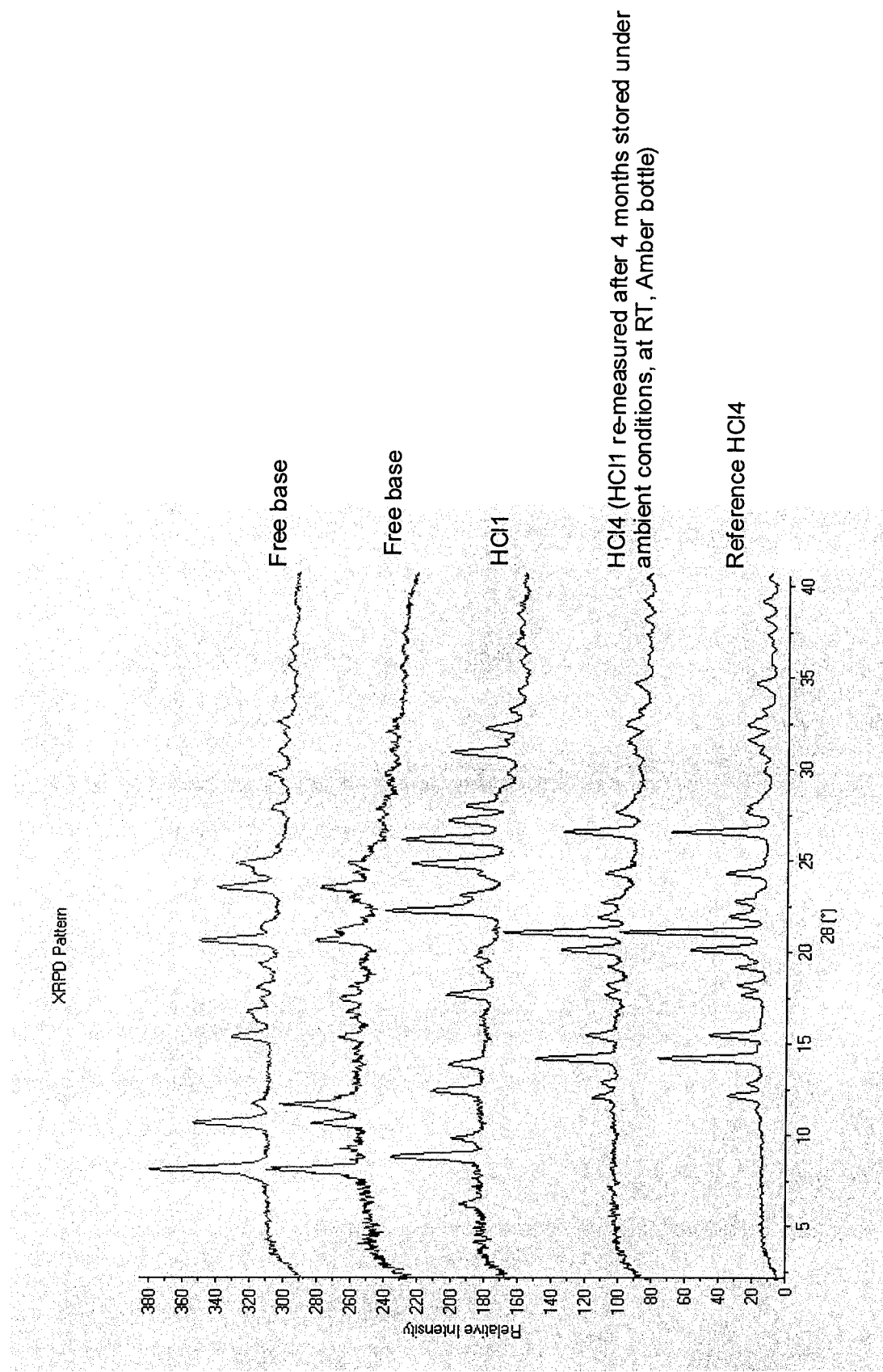

Figure 8B

| HCl4 Pos. [°2Th.] | d-spacing [Å] |
|---|---|
| 12.1 | 7.3 |
| 14.2 | 6.2 |
| 18.2 | 4.9 |
| 19.2 | 4.6 |
| 20.1 | 4.4 |
| 21.0 | 4.2 |
| 21.9 | 4.1 |
| 22.7 | 3.9 |
| 24.3 | 3.7 |
| 26.6 | 3.4 |
| 27.6 | 3.2 |
| 30.9 | 2.9 |
| 31.5 | 2.8 |
| 34.7 | 2.6 |
| 39.5 | 2.3 |

Figure 12B

| Form HCl3 | |
|---|---|
| Pos. [°2Th.] | d-spacing [Å] |
| 8.0 | 11.1 |
| 12.2 | 7.3 |
| 13.8 | 6.4 |
| 20.2 | 4.4 |
| 21.2 | 4.2 |
| 22.4 | 4.0 |
| 23.3 | 3.8 |
| 24.7 | 3.6 |
| 25.2 | 3.5 |
| 27.7 | 3.2 |
| 27.9 | 3.2 |
| 28.4 | 3.1 |
| 31.1 | 2.9 |
| 32.2 | 2.8 |
| 34.9 | 2.6 |

Figure 16B

| HCl2 Pos. [°2Th.] | d-spacing [Å] |
|---|---|
| 12.1 | 7.3 |
| 14.2 | 6.2 |
| 20.1 | 4.4 |
| 21.1 | 4.2 |
| 21.9 | 4.1 |
| 23.3 | 3.8 |
| 25.1 | 3.5 |
| 26.6 | 3.4 |
| 27.6 | 3.2 |

POLYMORPHS OF (S)-3-AMINOMETHYL-7-(3-HYDROXY-PROPOXY)-3H-BENZO[C][1,2]OXABOROL-1-OL

CROSS-REFERENCES TO RELATED APPLICATIONS

This application claims the benefit of U.S. Provisional Pat. App. No. 61/138,490, filed Dec. 17, 2008, each of which is incorporated by reference in its entirety for all purposes.

BACKGROUND OF THE INVENTION

The ability of a substance to exist in more than one crystalline form is defined as polymorphism and these different crystalline forms are named "polymorph modifications" or "polymorphs". In general, polymorphism is caused by the ability of the molecule of a substance to change its conformation or to form different intermolecular and intramolecular interactions, particularly hydrogen bonds, which is reflected in different atom arrangements in the crystal lattices of different polymorphs.

The different polymorphs of a substance possess different energies of the crystal lattice and, thus, they show different physical properties of the solid state such as form, density, melting point, colour, stability, dissolution rate, milling facility, granulation, compacting etc., which in medicaments may the preparation of pharmaceutical forms, their stability, dissolution and bioavailability and, consequently, their action.

Polymorphism of medicaments is the object of studies of interdisciplinary expert teams [J. Haleblian, W. McCrone, J. Pharm. Sci. 58 (1969) 911; L. Borka, Pharm. Acta Helv. 66 (1991) 16; M. Kuhnert-Brandstatter, Pharmazie 51 (1996) 443; H. G. Brittain, J. Pharm. Sci. 86 (1997) 405; W. H. Streng, DDT 2 (1997) 415; K. Yoshii, Chem. Pharm. Bull. 45 (1997) 338, etc.]. A good knowledge of polymorphism represents a precondition for a critical observation of the whole process of medicament development. Thus, at deciding on the production of a pharmaceutical form in solid state and with regard to the dose size, stability, dissolution and anticipated action, it is important to determine the existence of all solid state forms (on the market some computer programs can be found, e.g. >>Polymorph<< as a module of >>Cerius2<< program, MSI Inc., USA) and to determine the physical-chemical properties of each of them. Only on the basis of these determinations can the most appropriate polymorph be selected for the development of pharmaceutical formulations of desired properties.

The compound (S)-3-aminomethyl-7-(3-hydroxy-propoxy)-3H-benzo[c][1,2]oxaborol-1-ol is disclosed in the form of its hydrochloride salt in U.S. patent application Ser. No. 12/142,692 and has the following chemical structure:

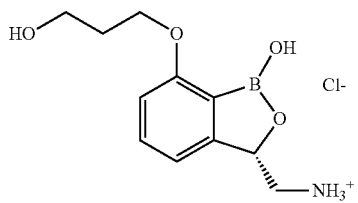 [SMILES: [NH3+]C[C@H]1OB(O)c2c(OCCCO)cccc21 ; [Cl-]]

(S)-3-Aminomethyl-7-(3-hydroxy-propoxy)-3H-benzo[c][1,2]oxaborol-1-ol has shown promise as an antibacterial agent, especially against Gram negative pathogens. Changes to the solid form of this compound that are capable of improving its physical and/or chemical stability gives a significant advantage over less stable forms of the same compound. The present invention advantageously provides one or more of those advantages and provides further related advantages.

SUMMARY OF THE INVENTION

This invention provides, among other things, crystalline polymorphs of the hydrochloride salt of (S)-3-aminomethyl-7-(3-hydroxy-propoxy)-3H-benzo[c][1,2]oxaborol-1-ol.

BRIEF DESCRIPTION OF THE DRAWINGS

FIG. 1B lists the 2θ values for the peaks in the XRPD pattern of FIG. 1A.

FIG. 2B lists the 2θ values for the peaks in the XRPD pattern of FIG. 2A.

FIG. 3B lists the 2θ values for the peaks in the XRPD pattern of FIG. 3A.

FIG. 4B lists the 2θ values for the peaks in the XRPD pattern of FIG. 4A.

FIG. 5 is a comparison of the free base form of (S)-3-aminomethyl-7-(3-hydroxy-propoxy)-3H-benzo[c][1,2]oxaborol-1-ol with polymorph form HCl1 and HCl4.

FIG. 8B lists the 2θ and d-spacing values for the peaks in the XRPD pattern of FIG. 8A.

FIG. 12B lists the 2θ and d-spacing values for the peaks in the XRPD pattern of FIG. 12A.

FIG. 16B lists the 2θ and d-spacing values for the peaks in the XRPD pattern of FIG. 16A.

DETAILED DESCRIPTION OF THE INVENTION

I. Definitions and Abbreviations

Figure 1A:
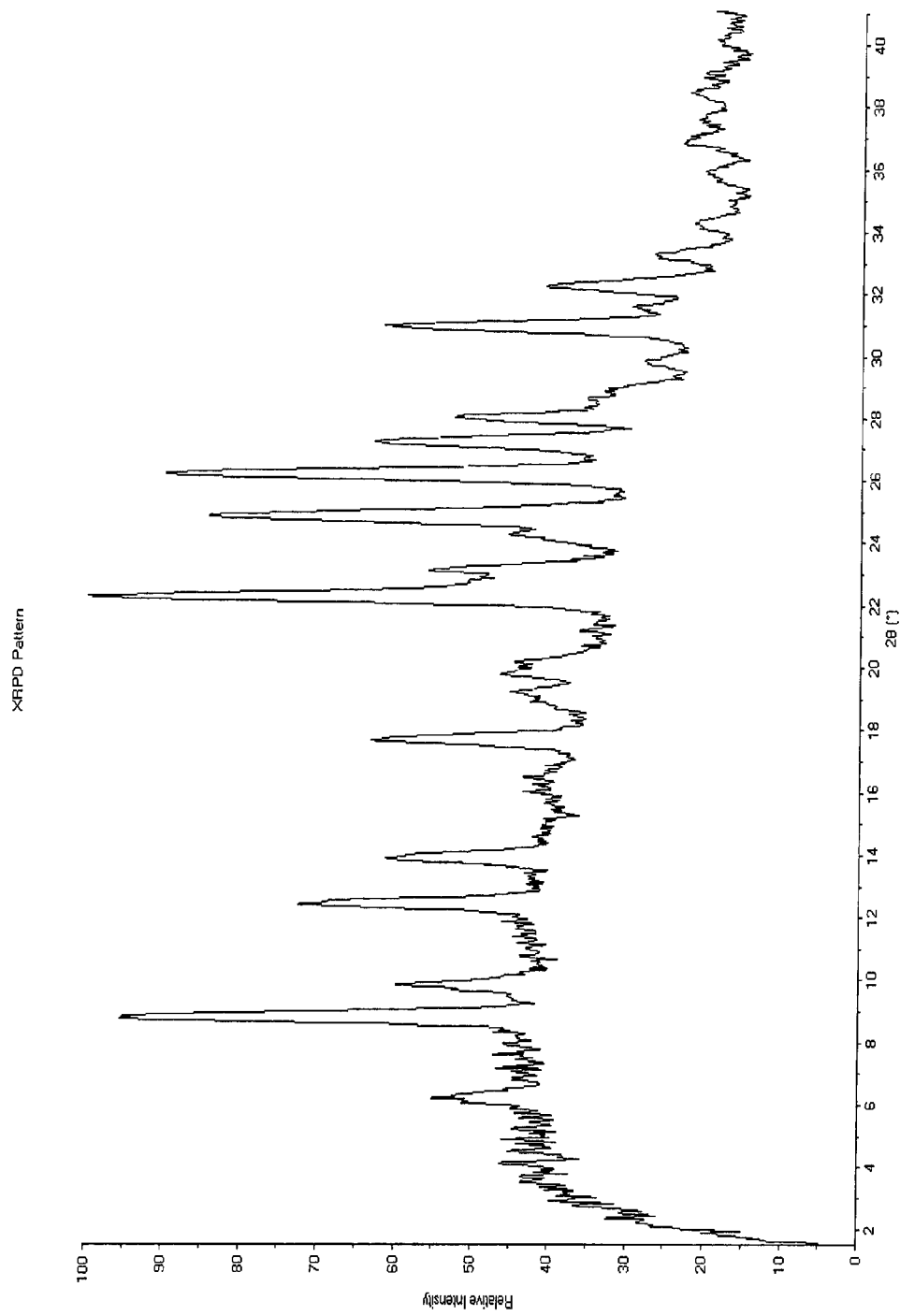
FIG. 1A is an X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl1.

The abbreviations used herein generally have their conventional meaning within the chemical and biological arts.

The following abbreviations have been used: aq.—aqueous; equiv—equivalent; Rt—room temperature; mp—melting point; $B_2pin_2$—bis(pinacolato)diboron; O/N—overnight; sat.—saturated; dppf—1,1'-Bis(diphenylphosphino)ferrocene; USP—United States Pharmacopeia; MTBE—methyl tert-butyl ether.

"Polymorph of the invention," as used herein refers to the polymorphs discussed herein as well as crystalline solvates and crystalline hydrates of these polymorphs.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents and/or vehicles used in formulating drug compositions effective for the desired use.

II. Introduction

It has been found that the hydrochloride salt of (S)-3-aminomethyl-7-(3-hydroxy-propoxy)-3H-benzo[c][1,2]oxaborol-1-ol in a specific polymorphic form provides one or more advantages. A synthesis of the hydrochloride salt of (S)-3-aminomethyl-7-(3-hydroxy-propoxy)-3H-benzo[c][1,2]oxaborol-1-ol has been described herein, as well as in U.S. patent application Ser. No. 12/142,692, which is incorporated by reference.

It is understood that all polymorphs described in this application are in a crystalline form. Therefore, the term 'polymorph' and 'crystalline polymorph' are equivalent.

Moreover it has been found that, depending on the choice of conditions which can be applied during the synthesis of (S)-3-aminomethyl-7-(3-hydroxy-propoxy)-3H-benzo[c][1,2]oxaborol-1-ol, the hydrochloride salt occurs in different modifications: polymorphs HCl1, HCl2, HCl3 and HCl4.

In an exemplary embodiment, the invention provides a polymorph of the invention. In an exemplary embodiment, the invention provides a polymorph described herein. In an exemplary embodiment, the invention provides a crystalline solvate of a polymorph described herein. In an exemplary embodiment, the invention provides a crystalline hydrate of a polymorph described herein. In an exemplary embodiment, the invention provides a crystalline solvate of polymorph form HCl4. In an exemplary embodiment, the invention provides a crystalline hydrate of polymorph form HCl4. In an exemplary embodiment, the invention provides a combination of two polymorphs of the invention. In an exemplary embodiment, the invention provides a combination of three polymorphs of the invention. In an exemplary embodiment, the invention provides a combination of four polymorphs of the invention. In an exemplary embodiment, the invention provides a combination of two polymorphs described herein, wherein one of the polymorphs is polymorph form HCl4. In an exemplary embodiment, the invention provides a combination of three polymorphs of the invention, wherein one of the polymorphs is polymorph form HCl4. In an exemplary embodiment, the invention provides a combination of four polymorphs of the invention, wherein one of the polymorphs is polymorph form HCl4.

The X-ray powder diffraction (XRPD) data for polymorph form HCl1, a hydrochloride salt (S)-3-aminomethyl-7-(3-hydroxy-propoxy)-3H-benzo[c][1,2]oxaborol-1-ol, was collected according to the details provided in Example 5. The XRPD pattern for polymorph form HCl1, and its 2-theta (2θ) values are shown in FIGS. 1A and 1B. In an exemplary embodiment, the invention provides polymorph form HCl1 having, upon XRPD analysis, any 10, any 9, any 8, any 7, any 6, any 5, any 4, any 3, any 2 or any 1 of the peaks shown in FIGS. 1A and 1B, ±2°2θ, ±1.7°2θ, ±1.5°2θ, ±1.2°2θ, ±1.0°2θ, ±0.9°2θ, ±0.8°2θ, ±0.7°2θ, ±0.6°2θ, ±0.5°2θ, ±0.4°2θ, ±0.3°2θ, ±0.2°2θ, or ±0.1°2θ.

Figure 2A:
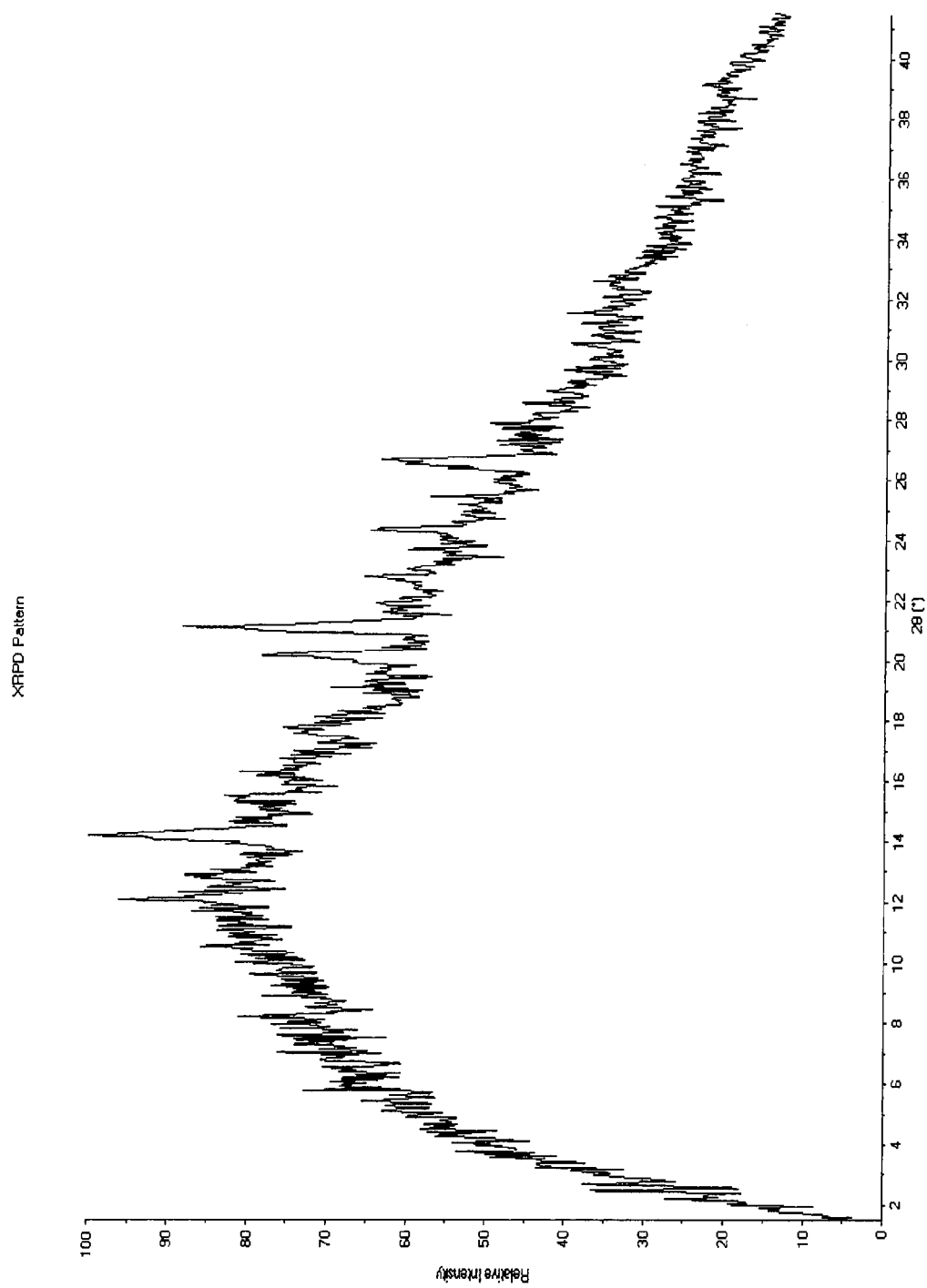
FIG. 2A is an X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl2. Polymorph form HCl2 has been shown with additional analysis, including Raman spectroscopy and thermal analysis, to be a mixture of two polymorphs HCl3 and HCl4.
Figure 2B:
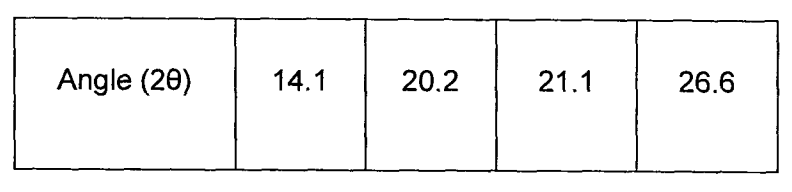

The XRPD pattern for another polymorph of (S)-3-aminomethyl-7-(3-hydroxy-propoxy)-3H-benzo[c][1,2]oxaborol-1-ol.HCl, referred to as polymorph form HCl2, and its 2-theta (2θ) values are shown in FIGS. 2A and 2B. After additional analysis was performed on the polymorph form HCl2 it was determined that this polymorph is a mixture of polymorph form HCl3 and polymorph form HCl4.

Figure 3A:
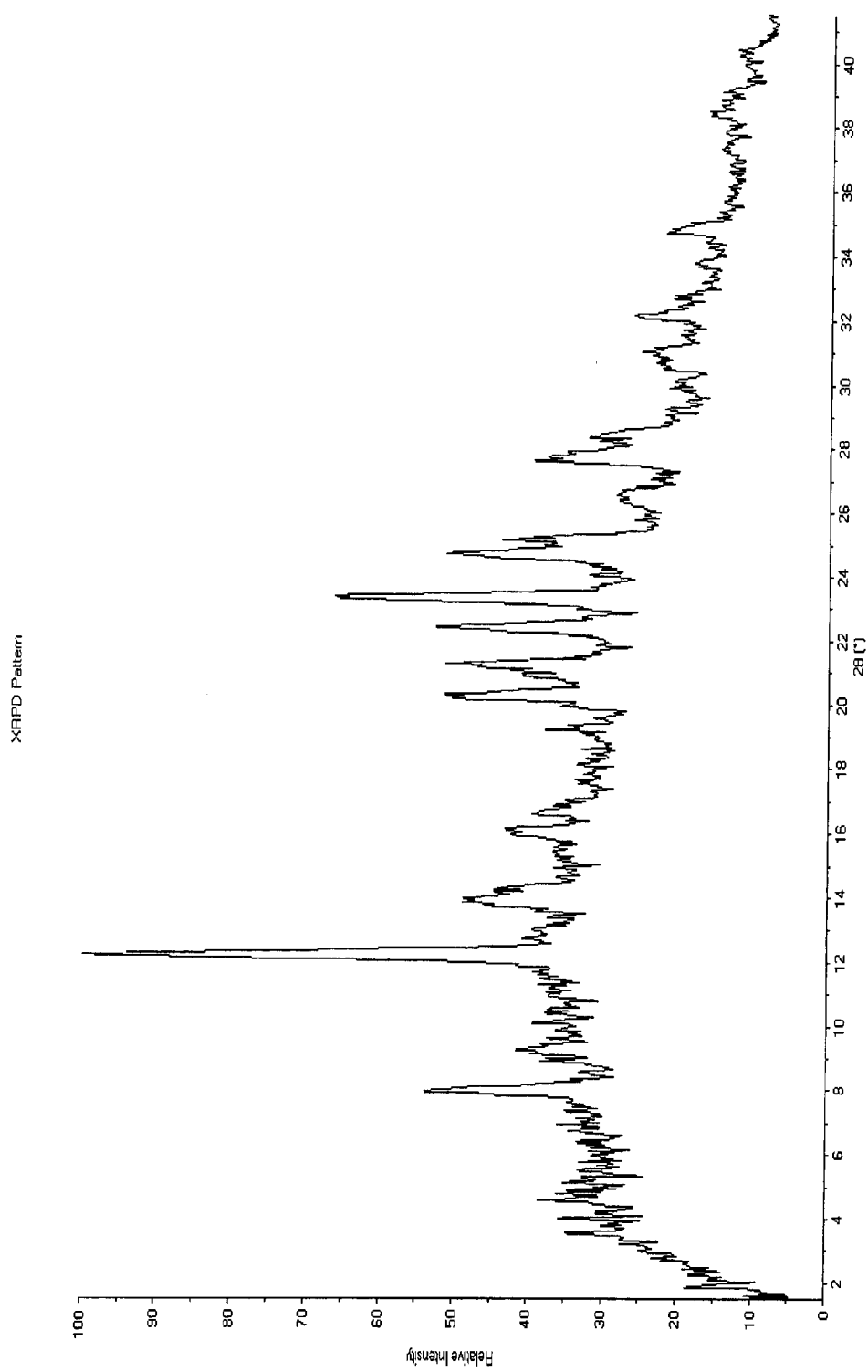
FIG. 3A is an X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl3.

The XRPD pattern for another polymorph of (S)-3-aminomethyl-7-(3-hydroxy-propoxy)-3H-benzo[c][1,2]oxaborol-1-ol.HCl, referred to as polymorph form HCl3, and its 2-theta (2θ) values are shown in FIGS. 3A and 3B. In an exemplary embodiment, the invention provides polymorph form HCl3 having, upon XRPD analysis, any 10, any 9, any 8, any 7, any 6, any 5, any 4, any 3, any 2 or any 1 of the peaks shown in FIGS. 3A and 3B, ±2°2θ, ±1.7°2θ, ±1.5°2θ, ±1.2°2θ, ±1.0°2θ, ±0.9°2θ, ±0.8°2θ, ±0.7°2θ, ±0.6°2θ, ±0.5°2θ, ±0.4°2θ, ±0.3°2θ, ±0.2°2θ, or ±0.1°2θ.

Figure 4A:
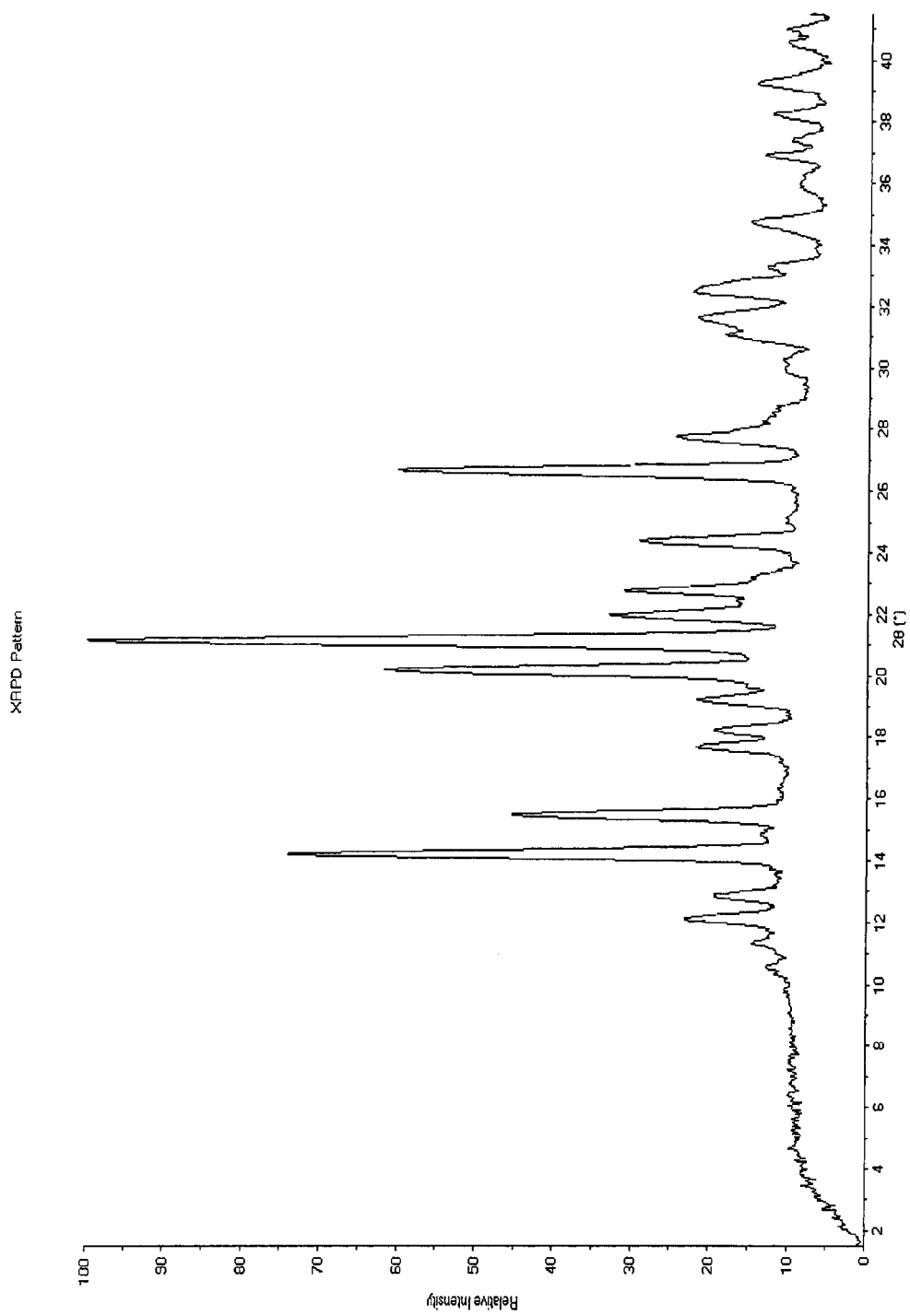
FIG. 4A is an X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl4.

The XRPD pattern for another polymorph of (S)-3-aminomethyl-7-(3-hydroxy-propoxy)-3H-benzo[c][1,2]oxaborol-1-ol.HCl, referred to as polymorph form HCl4, and its 2-theta (2θ) values are shown in FIGS. 4A and 4B. Additional studies, including a single crystal form screen, verify that HCl4 is the most stable polymorph of (S)-3-aminomethyl-7-(3-hydroxy-propoxy)-3H-benzo[c][1,2]oxaborol-1-ol.HCl. In an exemplary embodiment, the invention provides polymorph form HCl4 having, upon XRPD analysis, any 10, any 9, any 8, any 7, any 6, any 5, any 4, any 3, any 2 or any 1 of the peaks shown in FIGS. 1A and 1B, ±2°2θ, ±1.7°2θ, ±1.5°2θ, ±1.2°2θ, ±1.0°2θ, ±0.9°2θ, ±0.8°2θ, ±0.7°2θ, ±0.6°2θ, ±0.5°2θ, ±0.4°2θ, ±0.3°2θ, ±0.2°2θ, or ±0.1°2θ. In an exemplary embodiment, the invention provides polymorph form HCl4 having, upon XRPD analysis, any 10 of the peaks shown in FIGS. 4A and 4B, ±2°2θ, ±1.7°2θ, ±1.5°2θ, ±1.2°2θ, ±1.0°2θ, ±0.9°2θ, ±0.8°2θ, ±0.7°2θ, ±0.6°2θ, ±0.5°2θ, ±0.4°2θ, ±0.3°2θ, ±0.2°2θ, or ±0.1°2θ. In an exemplary embodiment, the invention provides polymorph form HCl4 having, upon XRPD analysis, any 10 of the peaks shown in FIGS. 4A and 4B, ±1.0°2θ. In an exemplary embodiment, the invention provides polymorph form HCl4 having, upon XRPD analysis, any 10 of the peaks shown in FIGS. 4A and 4B, ±0.5°2θ. In an exemplary embodiment, the invention provides polymorph form HCl4 having, upon XRPD analysis, any 8 of the peaks shown in FIGS. 4A and 4B, ±1.0°2θ. In an exemplary embodiment, the invention provides polymorph form HCl4 having, upon XRPD analysis, any 8 of the peaks shown in FIGS. 4A and 4B, ±0.5°2θ. In an exemplary embodiment, the invention provides polymorph form HCl4 having, upon XRPD analysis, any 5 of the peaks shown in FIGS. 4A and 4B, ±1.0°2θ. In an exemplary embodiment, the invention provides polymorph form HCl4 having, upon XRPD analysis, any 3 of the peaks shown in FIGS. 4A and 4B, ±1.0°2θ. In an exemplary embodiment, the invention provides polymorph form HCl4 having, upon XRPD analysis, any 3 of the peaks shown in FIGS. 4A and 4B, ±0.5°2θ.

A comparison of the free base form of (S)-3-aminomethyl-7-(3-hydroxy-propoxy)-3H-benzo[c][1,2]oxaborol-1-ol with polymorph form HCl1 and HCl4 is shown in FIG. 5. Raman spectroscopy (FIG. 6), additional XRPD analysis (FIGS. 7, 8A and 8B), differential scanning calorimety (DCS) (FIG. 9) and thermogravimetric analysis (TGA) (FIG. 10) of polymorph form HCl4 are shown and discussed in Examples 4 through 8. Polymorph form HCl4 for these analyses was prepared according to Examples 2, Methods A and B, and Example 4.

In an exemplary embodiment, the invention provides a polymorph having, upon X-ray crystallographic analysis, crystal parameters similar to those described herein. In an exemplary embodiment, the invention provides a polymorph having, upon X-ray crystallographic analysis, an orthorhombic crystallographic system. In an exemplary embodiment, the invention provides polymorph form HCl4 having, upon X-ray crystallographic analysis, an orthorhombic crystallographic system. In an exemplary embodiment, the invention provides a polymorph having, upon X-ray crystallographic analysis, a $P2_12_12_1$ space group. In an exemplary embodiment, the invention provides polymorph form HCl4 having, upon X-ray crystallographic analysis, a $P2_12_12_1$ space group. In an exemplary embodiment, the invention provides a polymorph having, upon X-ray crystallographic analysis, crystal dimensions of a=about 9.1045(2) Å, b=about 10.3107(2) Å, c=about 14.5988(3) Å, α=about 90.00°, β=about 90.00°, γ=about 90.00°. In an exemplary embodiment, the invention provides polymorph form HCl4 having, upon X-ray crystallographic analysis, crystal dimensions of a=about 9.1045(2) Å, b=about 10.3107(2) Å, c=about 14.5988(3) Å, α=about 90.00°, β=about 90.00°, γ=about 90.00°. In an exemplary embodiment, the invention provides a polymorph having, upon X-ray crystallographic analysis, a crystal volume of 1370.44(5) Å$^3$. In an exemplary embodiment, the invention provides polymorph form HCl4 having, upon X-ray crystallographic analysis, a crystal volume of 1370.44(5) Å$^3$. In an exemplary embodiment, the invention provides a polymorph having, upon X-ray crystallographic analysis, Z and calculated density values of about 4 and about 1.326 g cm$^{-3}$, respectively. In an exemplary embodiment, the invention provides polymorph form HCl4 having, upon X-ray crystallographic analysis, Z and calculated density values of about 4 and about 1.326 g cm$^{-3}$, respectively. In an exemplary embodiment, the invention provides a polymorph having, upon X-ray crystallographic analysis, crystal parameters of substantially the following values:

Crystallographic system: orthorhombic
Space group: $P2_12_12_1$
Crystal dimensions: a=9.1045(2) Å, b=10.3107(2) Å, c=14.5988(3) Å α=90.00°, β=90.00°, γ=90.00°
Volume 1370.44(5) Å$^3$
Z, calculated density: 4, 1.326 g cm$^{-3}$.

Figure 6:
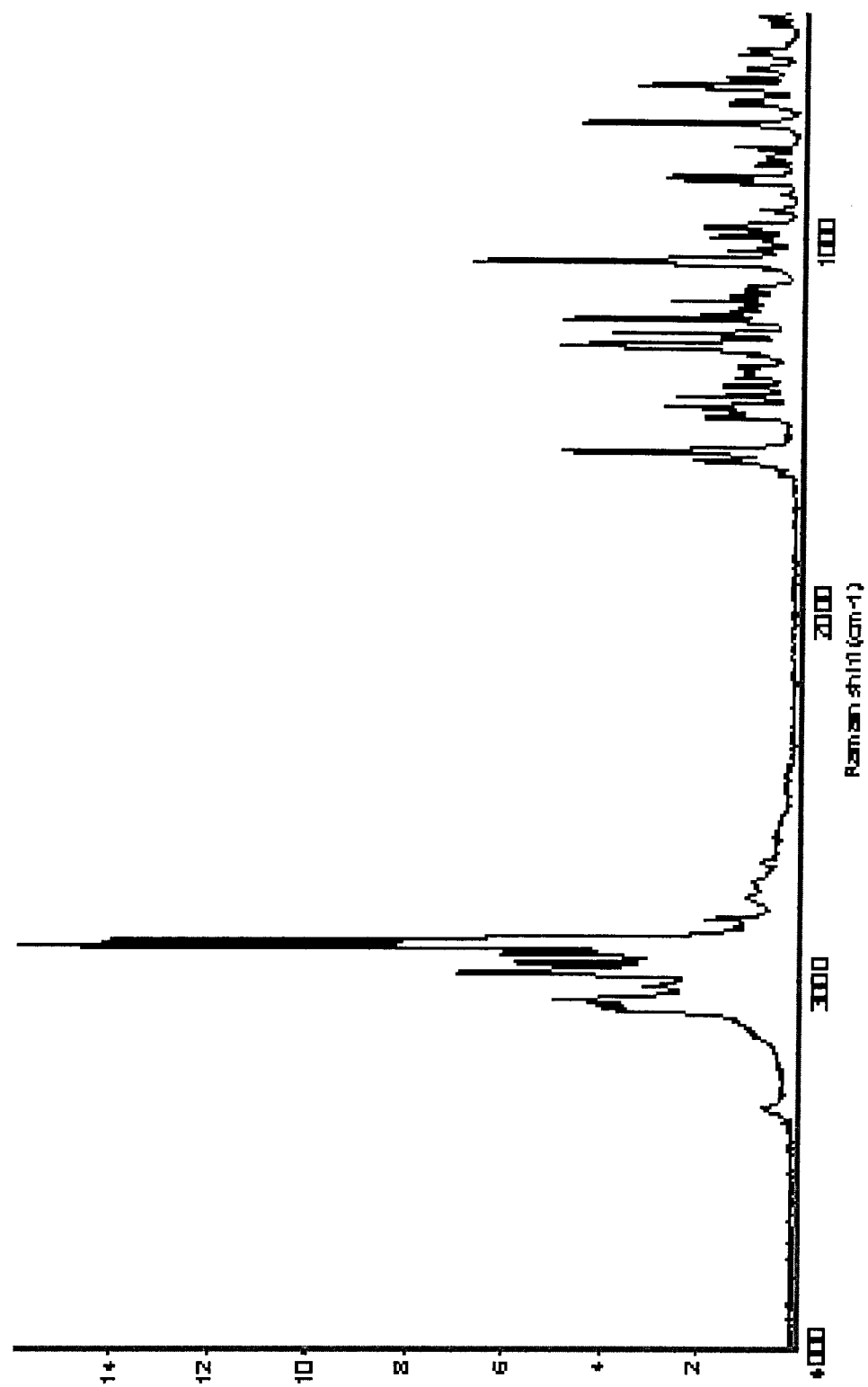
FIG. 6 is a Raman spectroscopy analysis of the hydrochloride salt of (S)-3-aminomethyl-7-(3-hydroxy-propoxy)-3H-benzo[c][1,2]oxaborol-1-ol referred to as polymorph form HCl4.

In an exemplary embodiment, the invention provides a polymorph having, upon Raman spectroscopic analysis, peaks substantially as described herein, such as in FIG. 6, a Fourier-Transform infrared spectrum obtained using a Nicolet NXR 9650 FT-Raman Spectrometer at a resolution of 4 cm$^{-1}$ with excitation from a Nd:YVO4 laser (λ=1064 nm). In an exemplary embodiment, the invention provides a polymorph having, upon Raman spectroscopic analysis, any 15, any 14, any 13, any 12, any 10, any 11, any 9, any 8, any 7, any 6, any 5, any 4, any 3, any 2 or any 1 of the peaks having substantially the following wavenumbers (cm$^1$) selected from the group: 3076.4, 3054.6, 2987.4, 2975.5, 2954.2, 2928.0, 2909.8, 2896.0, 1578.6, 1298.2, 1291.6, 1263.0, 1226.8, 1068.9, 694.9, ±50 wavenumbers, ±45 wavenumbers, ±40 wavenumbers, ±35 wavenumbers, ±30 wavenumbers, ±25 wavenumbers, ±20 wavenumbers, ±15 wavenumbers, ±10 wavenumbers, or ±5 wavenumbers. In related particular embodiments, the entire list of peaks as described, or any subset thereof, is sufficient to characterize polymorph form HCl4. A particular embodiment provides a polymorph having Raman spectroscopic wavenumbers ($cm^{-1}$) of 10 or more peaks of the above list. Another particular embodiment provides a polymorph having spectroscopic wavenumbers ($cm^{-1}$) of 7 or more peaks of the above list. Another particular embodiment provides a polymorph having spectroscopic wavenumbers ($cm^{-1}$) of 5 or more peaks of the above list. Still another particular embodiment provides a polymorph having spectroscopic wavenumbers ($cm^{-1}$) of 4 or more peaks of the above list.

Figure 7:
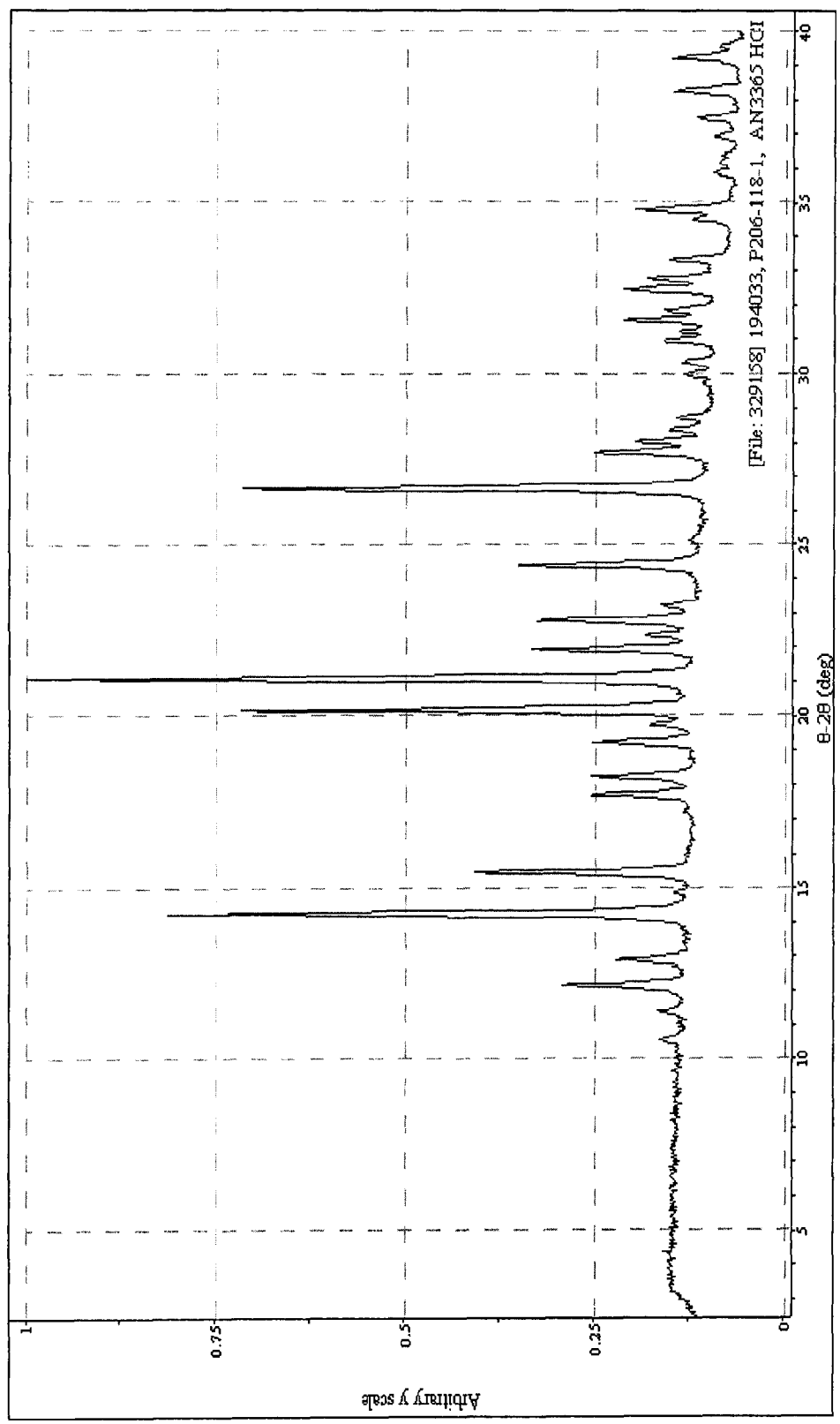
FIG. 7 is another X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl4, obtained using a sample of polymorph form HCl4 prepared according to Example 2, Method A.
Figure 8A:
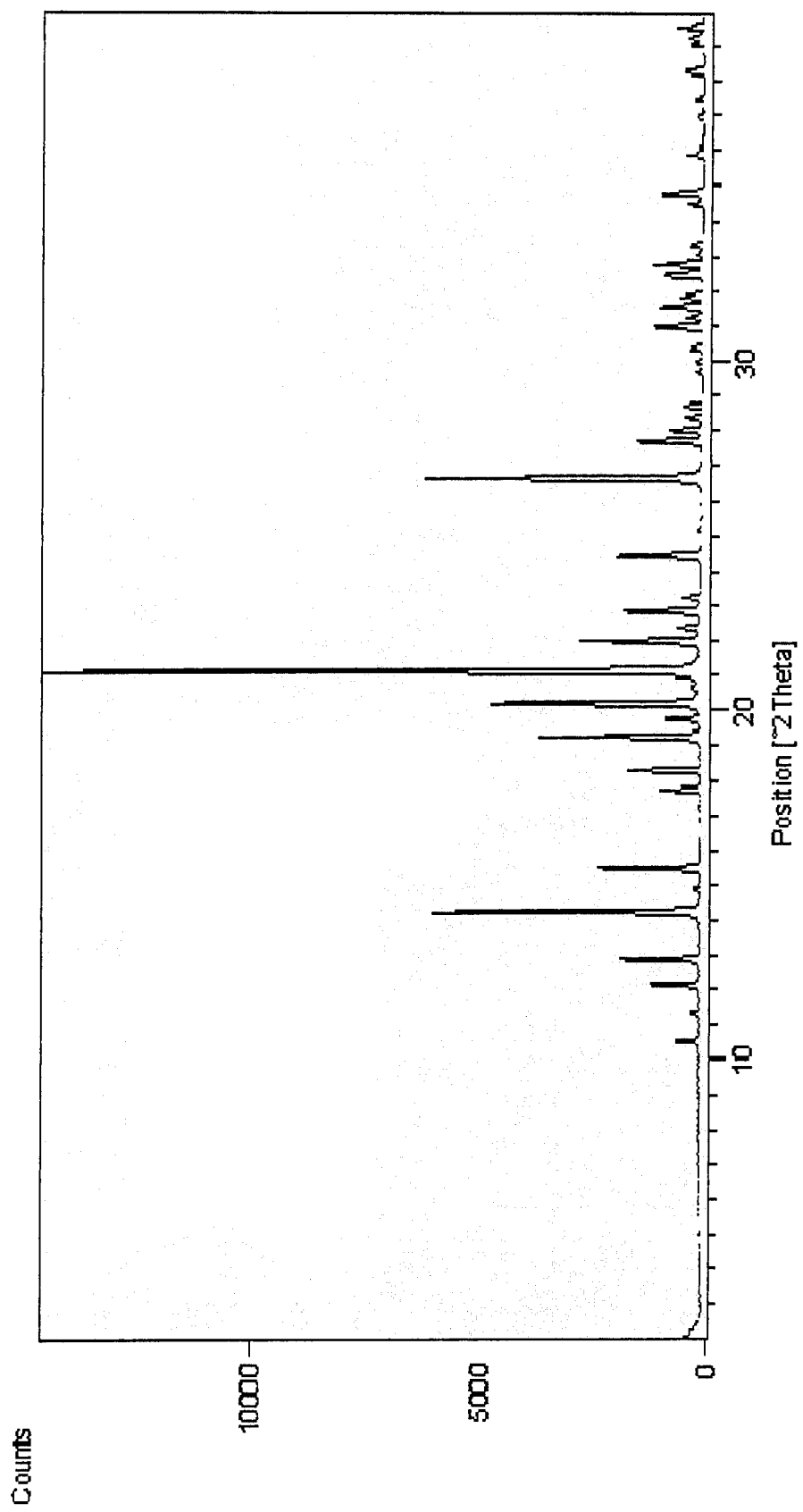
FIG. 8A is another X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl4, obtained using a sample of polymorph form HCl4 prepared according to Example 2, Method B.

In another exemplary embodiment, the invention provides a polymorph having an XRPD pattern substantially as depicted in any of FIG. 4A, 7 or 8A. In another exemplary embodiment, the invention provides a polymorph having substantially the peaks listed in FIG. 8B, and the corresponding d-spacing values. In particular embodiments, there is provided a polymorph having XRPD peaks selected from any 15, any 14, any 13, any 12, any 11, any 10, any 9, any 8, any 7, any 6, any 5, any 3, and 2 or any 1 of the peaks having substantially the 2θ values selected from the group: 12.1, 14.2, 18.2, 19.2, 20.1, 21.0, 21.9, 22.7, 24.3, 26.6, 27.6, 30.9, 31.5, 34.7, or 39.5. In a more particular embodiment, there is provided a polymorph having the entire list of peaks, or any subset thereof, as listed in FIG. 8B. In another particular embodiment, there is provided a polymorph having XRPD 2θ values of any 10 or more peaks, or any 7 or more peaks, or any 5 or more peaks, or any 4 or more peaks, listed above, and/or as shown in FIG. 8A or listed in FIG. 8B. In related particular embodiments, the polymorph may have any 1 or more of the d-spacings listed in FIG. 8B.

It has been found that these different modifications can be deliberately produced by a suitable choice of reaction conditions.

In an exemplary embodiment, the polymorph is produced by evaporation and/or recrystallization from a solution with a concentration of (S)-3-aminomethyl-7-(3-hydroxy-propoxy)-3H-benzo[c][1,2]oxaborol-1-ol.HCl of about 11 mg/mL or greater. In an exemplary embodiment, the concentration of (S)-3-aminomethyl-7-(3-hydroxy-propoxy)-3H-benzo[c][1,2]oxaborol-1-ol.HCl is about 15 mg/mL or greater. In an exemplary embodiment, the concentration of (S)-3-aminomethyl-7-(3-hydroxy-propoxy)-3H-benzo[c][1,2]oxaborol-1-ol.HCl is about 20 mg/mL or greater. In an exemplary embodiment, the concentration of (S)-3-aminomethyl-7-(3-hydroxy-propoxy)-3H-benzo[c][1,2]oxaborol-1-ol.HCl is about 22 mg/mL or greater. In an exemplary embodiment, the concentration of (S)-3-aminomethyl-7-(3-hydroxy-propoxy)-3H-benzo[c][1,2]oxaborol-1-ol.HCl is from about 11 mg/mL to about 30 mg/mL. In an exemplary embodiment, according to any of the above paragraphs, the concentration of (S)-3-aminomethyl-7-(3-hydroxy-propoxy)-3H-benzo[c][1,2]oxaborol-1-ol.HCl is from about 15 mg/mL to about 50 mg/mL. In an exemplary embodiment, according to any of the above paragraphs, the concentration of (S)-3-aminomethyl-7-(3-hydroxy-propoxy)-3H-benzo[c][1,2]oxaborol-1-ol.HCl is from about 15 mg/mL to about 500 mg/mL. In an exemplary embodiment, the solution comprises an alcohol. In an exemplary embodiment, the solution comprises methanol. In an exemplary embodiment, the solution comprises ethanol. In an exemplary embodiment, the solution comprises an aliphatic compound. In an exemplary embodiment, the solution comprises pentane.

It has been found that the HCl4 polymorph, which can be obtained in crystalline form by choosing specific reaction conditions, provides one or more of the advantages mentioned herein. Accordingly in one aspect, the present invention relates to polymorph form HCl4 of (S)-3-aminomethyl-7-(3-hydroxy-propoxy)-3H-benzo[c][1,2]oxaborol-1-ol.HCl. The polymorph form HCl4 of (S)-3-aminomethyl-7-(3-hydroxy-propoxy)-3H-benzo[c][1,2]oxaborol-1-ol.HCl exhibits increased stability when compared to other polymorphs of (S)-3-aminomethyl-7-(3-hydroxy-propoxy)-3H-benzo[c][1,2]oxaborol-1-ol.HCl. In an exemplary embodiment, the stability is physical stability. In an exemplary embodiment, the stability is chemical stability.

According to another aspect, the present invention relates to a process for producing a purified version of the HCl4 polymorph of (S)-3-aminomethyl-7-(3-hydroxy-propoxy)-3H-benzo[c][1,2]oxaborol-1-ol.HCl.

In another aspect, the invention provides a method of treating a disease in an animal suffering from the disease, comprising: administering to the animal a therapeutically effective amount of a polymorph described herein, thereby treating the disease. In an exemplary embodiment, the disease is associated with a bacteria. In an exemplary embodiment, the bacteria is a Gram negative bacteria. In an exemplary embodiment, the Gram negative bacteria is selected from the group consisting of *Neisseria* species, *Escherichia* species, *Shigella* species, *Salmonella* species, *Yersinia* species, *Klebsiella* species, *Proteus* species, *Enterobacter* species, *Serratia* species, *Vibrio* species, *Campylobacter* species, *Helicobacter* species, *Pseudomonas* species, *Bacteroides* species, *Haemophilus* species, *Bordetella* species, *Legionella* species, *Francisella* species, *Brucella* species, *Pasteurella* species, *Gardnerella* species, *Spirochetes* species, *Chlamydia* species, *Rickettsiae* species. In an exemplary embodiment, the bacteria is a *Mycoplasma pneumoniae* and *Ureaplasma urealyticum*. In an exemplary embodiment, the disease is selected from the group consisting of meningitis, gonorrhea, otitis, otitis extema, folliculitis, diarrhea, urinary tract infections, sepsis, HAP, bacteremia, endocarditis, gastroenteritis, Typhoid fever, supsis, endocarditis, sinusitis, bubonic plague, enteric fever, hospital-acquired infection, skin and skin-structure infection, pneumonia, cholera, chronic gastritis, osteomylitis, burn-wound infections, corneal infections, periodontal disease, aspriation pneumonia, piglottitis, septic arthritis, chancroid, vaginitis, whooping cough, pontiac fever, tularemia, brucellosis, syphilis, Lyme disease, chlamydia, Rocky Mountain spotted fever, typhus, tracheobronchitis, walking pneumonia, urethritis, pyelonenephritis, intra-abdominal infection, febrile neutropenia, pelvic infection, bacteraemia and septicaemia. In an exemplary embodiment, the disease is pneumonia. In an exemplary embodiment, the polymorph is polymorph form HCl4 of (S)-3-aminomethyl-7-(3-hydroxy-propoxy)-3H-benzo[c][1,2]oxaborol-1-ol-.HCl. In an exemplary embodiment, the polymorph has substantially similar X-ray crystallographic values to those described herein. In an exemplary embodiment, the polymorph has substantially similar Raman spectroscopic values to those described herein. In an exemplary embodiment, the polymorph has substantially similar X-ray powder diffraction patterns to those described herein.

A further aspect of the present invention relates to a pharmaceutical composition which comprises: a) polymorph of the hydrochloride salt of (S)-3-aminomethyl-7-(3-hydroxy-propoxy)-3H-benzo[c][1,2]oxaborol-1-ol and b) at least one excipient or carrier. In an exemplary embodiment, the polymorph is polymorph form HCl4 of (S)-3-aminomethyl-7-(3-hydroxy-propoxy)-3H-benzo[c][1,2]oxaborol-1-ol.HCl. In an exemplary embodiment, the polymorph has substantially similar X-ray crystallographic values to those described herein. In an exemplary embodiment, the polymorph has substantially similar Raman spectroscopic values to those described herein. In an exemplary embodiment, the polymorph has substantially similar X-ray powder diffraction patterns to those described herein. This pharmaceutical composition is useful for treating disease involving bacteria. In an exemplary embodiment, the polymorph is described herein. In an exemplary embodiment, the bacteria is described herein. In an exemplary embodiment, the disease is described herein.

A further aspect of the present invention relates to the use of a polymorph of (S)-3-aminomethyl-7-(3-hydroxy-propoxy)-3H-benzo[c][1,2]oxaborol-1-ol.HCl for preparing a pharmaceutical composition for treating bacterial diseases in which the use of compounds displaying affinity for the leucyl tRNA synthetase of the bacteria may have a therapeutic benefit.

A further aspect of the present invention relates to the use of the HCl4 polymorph of (S)-3-aminomethyl-7-(3-hydroxy-propoxy)-3H-benzo[c][1,2]oxaborol-1-ol.HCl for preparing a pharmaceutical composition.

In particular, the instant invention relates to the use of the HCl4 polymorph of (S)-3-aminomethyl-7-(3-hydroxy-propoxy)-3H-benzo[c][1,2]oxaborol-1-ol.HCl for the preparation of a medicament for the treatment of a disease described herein. In an exemplary embodiment, the disease is associated with a Gram negative bacteria.

Particular preferred according to the invention is the use of the HCl4 polymorph of (S)-3-aminomethyl-7-(3-hydroxy-propoxy)-3H-benzo[c][1,2]oxaborol-1-ol.HCl for the preparation of a medicament for the treatment of a disease selected herein.

As a further feature of the present invention there are provided pharmaceutical compositions comprising as an active ingredient a polymorph of (S)-3-aminomethyl-7-(3-hydroxy-propoxy)-3H-benzo[c][1,2]oxaborol-1-ol.HCl in addition with at least one pharmaceutical carrier. For pharmaceutical administration, the polymorph of (S)-3-aminomethyl-7-(3-hydroxy-propoxy)-3H-benzo[c][1,2]oxaborol-1-ol.HCl may be incorporated into the conventional pharmaceutical preparation in solid, liquid, ointment, cream, suspension or spray form. The composition may, for example, be presented in a form suitable for oral, rectal, parenteral administration or for nasal inhalation: preferred forms include for example, capsules, tablets, coated tablets, ampoules, suppositories and nasal spray. The active ingredient may be incorporated in excipients or carriers conventionally used in pharmaceutical compositions such as, for example, talc, arabic gum, lactose, gelatine, magnesium stearate, corn starch, aqueous or non aqueous vehicles, polyvynil pyrrolidone, semisynthetic glycerides of fatty acids, benzalconium chloride, sodium phosphate, EDTA, polysorbate 80. The compositions are advantageously formulated in dosage units, each dosage unit being adapted to supply a single dose of the active ingredient. Each dosage unit may conveniently contain from 0.01 mg to 100 mg, preferably from 0.1 to 50 mg.

Exemplary embodiments are summarized herein below.

One particular embodiment provides a polymorph of a hydrochloride salt of (S)-3-aminomethyl-7-(3-hydroxy-propoxy)-3H-benzo[c][1,2]oxaborol-1-ol, characterized by having any of the peaks of XRPD pattern (1) as shown in FIG. 8A.

Another particular embodiment provides a polymorph comprising any 4 peaks as depicted in XRPD pattern 1. Still another exemplary embodiment provides a polymorph comprising any 7 peaks as depicted in XRPD pattern 1. A more particular embodiment provides a polymorph comprising any 10 peaks as depicted in XRPD pattern 1. Still another more particular embodiment provides a polymorph comprising all peaks as depicted in XRPD pattern 1.

Another exemplary embodiment provides a polymorph polymorph of a hydrochloride salt of (S)-3-aminomethyl-7-(3-hydroxy-propoxy)-3H-benzo[c][1,2]oxaborol-1-ol wherein the polymorph is characterized by having any of the 2θ values listed in Table 1, ±2°2θ, ±1.7°2θ, ±1.5°2θ, ±1.2°2θ, ±1.0°2θ, ±0.9°2θ, ±0.8°2θ, ±0.7°2θ, ±0.6°2θ, ±0.5°2θ, ±0.4°2θ, ±0.3°2θ, ±0.2°2θ, or ±0.1°2θ as shown in FIG. 8B.

Another exemplary embodiment provides a polymorph polymorph of a hydrochloride salt of (S)-3-aminomethyl-7-(3-hydroxy-propoxy)-3H-benzo[c][1,2]oxaborol-1-ol wherein the polymorph is characterized by having any of the 2θ values listed in Table 2, ±2°2θ, ±1.7°2θ, ±1.5°2θ, ±1.2°2θ, ±1.0°2θ, ±0.9°2θ, ±0.8°2θ, ±0.7°2θ, ±0.6°2θ, ±0.5°2θ, ±0.4°2θ, ±0.3°2θ, ±0.2°2θ, or ±0.1°2θ:

TABLE 2

| Pos. [°2θ.] |
| --- |
| 12.1 |
| 14.2 |
| 18.2 |
| 19.2 |
| 20.1 |
| 21.0 |
| 21.9 |
| 22.7 |
| 24.3 |
| 26.6 |
| 27.6 |
| 30.9 |
| 31.5 |
| 34.7 |
| 39.5 |

Still another exemplary embodiment provides a polymorph of a hydrochloride salt of (S)-3-aminomethyl-7-(3-hydroxy-propoxy)-3H-benzo[c][1,2]oxaborol-1-ol having, upon X-ray crystallographic analysis, crystal parameters of substantially the following values:
Crystallographic system: orthorhombic
Space group: $P2_12_12_1$
Crystal dimensions: a=9.1045(2) Å, b=10.3107(2) Å, c=14.5988(3) Å α=90.00°, β=90.00°, γ=90.00°
Volume 1370.44(5) Å$^3$
Z, calculated density 4, 1.326 g cm$^{-3}$.

Another exemplary embodiment provides a polymorph of a hydrochloride salt of (S)-3-aminomethyl-7-(3-hydroxy-propoxy)-3H-benzo[c][1,2]oxaborol-1-ol, characterized by having any of the peaks of Raman spectrum (1) as shown in FIG. 6.

Yet another exemplary embodiment provides a pharmaceutical composition comprising a polymorph as described and at least one excipient or carrier.

Another exemplary embodiment provides a method for treating a disease in an animal suffering from said disease, comprising administering to the animal a therapeutically effective amount of a polymorph as described herein, wherein said disease is associated with a bacteria.

Yet another exemplary embodiment provides a method for treating a disease in an animal suffering from a disease as described wherein the bacteria is a Gram negative bacteria.

In another exemplary embodiment, there is provided a method for treating a disease in an animal suffering from said disease as described, wherein the bacteria is selected from the group consisting of *Neisseria* species, *Escherichia* species, *Shigella* species, *Salmonella* species, *Yersinia* species, *Klebsiella* species, *Proteus* species, *Enterobacter* species, *Serratia* species, *Vibrio* species, *Campylobacter* species, *Helicobacter* species, *Pseudomonas* species, *Bacteroides* species, *Haemophilus* species, *Bordetella* species, *Legionella* species, *Francisella* species, *Brucella* species, *Pasteurella* species, *Gardnerella* species, *Spirochetes* species, *Chlamydia* species and *Rickettsiae* species.

Still another exemplary embodiment provides a method for treating a disease in an animal suffering from said disease as described, wherein the disease is selected from the group consisting of meningitis, gonorrhea, otitis, otitis extema, folliculitis, diarrhea, urinary tract infections, sepsis, HAP, bacteremia, endocarditis, gastroenteritis, Typhoid fever, supsis, endocarditis, sinusitis, bubonic plague, enteric fever, hospital-acquired infection, skin and skin-structure infection, pneumonia, cholera, chronic gastritis, osteomylitis, burn-wound infections, corneal infections, periodontal disease, aspriation pneumonia, piglottitis, septic arthritis, chancroid, vaginitis, whooping cough, pontiac fever, tularemia, brucellosis, syphilis, Lyme disease, chlamydia, Rocky Mountain spotted fever, typhus, tracheobronchitis, walking pneumonia, urethritis, pyelonenephritis, intra-abdominal infection, febrile neutropenia, pelvic infection, bacteraemia and septicaemia.

Yet another exemplary embodiment provides a method for treating a disease in an animal suffering from said disease as described, wherein the disease is pneumonia.

Another exemplary embodiment provides crystalline (S)-3-aminomethyl-7-(3-hydroxy-propoxy)-3H-benzo[c][1,2]oxaborol-1-ol.HCl, form HCl4. Another exemplary embodiment provides crystalline (S)-3-aminomethyl-7-(3-hydroxy-propoxy)-3H-benzo[c][1,2]oxaborol-1-ol.HCl, form HCl3. Another exemplary embodiment provides crystalline (S)-3-aminomethyl-7-(3-hydroxy-propoxy)-3H-benzo[c][1,2]oxaborol-1-ol.HCl, form HCl2. Another exemplary embodiment provides crystalline (S)-3-aminomethyl-7-(3-hydroxy-propoxy)-3H-benzo[c][1,2]oxaborol-1-ol.HCl, form HCl1. Still another exemplary embodiment provides a method of preparing crystalline (S)-3-aminomethyl-7-(3-hydroxy-propoxy)-3H-benzo[c][1,2]oxaborol-1-ol.HCl, form HCl4, HCl3, HCl2, HCl1 as described above.

Additional exemplary embodiments are summarized herein below.

In an exemplary embodiment, the invention is a crystalline polymorph characterized by having essentially any of the °2θ values listed in Table 1±0.2°2θ:

TABLE 1

| Pos. [°2θ] | d-spacing [Å] |
|---|---|
| 12.1 | 7.3 |
| 14.2 | 6.2 |
| 18.2 | 4.9 |
| 19.2 | 4.6 |
| 20.1 | 4.4 |
| 21.0 | 4.2 |
| 21.9 | 4.1 |
| 22.7 | 3.9 |
| 24.3 | 3.7 |
| 26.6 | 3.4 |
| 27.6 | 3.2 |
| 30.9 | 2.9 |
| 31.5 | 2.8 |

TABLE 1-continued

| Pos. [°2θ] | d-spacing [Å] |
|---|---|
| 34.7 | 2.6 |
| 39.5 | 2.3 |

In an exemplary embodiment, according to the above paragraph, comprising any 4 peaks, ±0.2°2θ, as depicted in Table 1.

In an exemplary embodiment, according to any of the above paragraphs, comprising any 7 peaks, ±0.2°2θ, as depicted in Table 1.

In an exemplary embodiment, according to any of the above paragraphs, comprising any 10 peaks, ±0.2°2θ, as depicted in Table 1.

In an exemplary embodiment, according to any of the above paragraphs, comprising all peaks, ±0.2°2θ, as depicted in Table 1.

In an exemplary embodiment, the invention is a crystalline polymorph of a hydrochloride salt of (S)-3-aminomethyl-7-(3-hydroxy-propoxy)-3H-benzo[c][1,2]oxaborol-1-ol, characterized by having essentially any of the peaks of XRPD pattern 1±0.2°2θ as shown in FIG. 8A.

In an exemplary embodiment, the invention is a crystalline polymorph of a hydrochloride salt of (S)-3-aminomethyl-7-(3-hydroxy-propoxy)-3H-benzo[c][1,2]oxaborol-1-ol having, upon X-ray crystallographic analysis, crystal parameters of substantially the following values:

Crystallographic system: orthorhombic
Space group: $P2_12_12_1$
Crystal dimensions: a=9.1045(2) Å, b=10.3107(2) Å, c=14.5988(3) Å α=90.00°, β=90.00°, γ=90.00°
Volume 1370.44(5) Å$^3$
Z, calculated density 4, 1.326 g cm$^{-3}$.

In an exemplary embodiment, the invention is a crystalline polymorph of a hydrochloride salt of (S)-3-aminomethyl-7-(3-hydroxy-propoxy)-3H-benzo[c][1,2]oxaborol-1-ol, characterized by having any of the peaks, ±50 wavenumbers (cm$^{-1}$) of Raman spectrum (1) as shown in FIG. 6.

In an exemplary embodiment, according to the above paragraph, wherein the crystalline polymorph has a multiplet of peaks between about 2800 and about 3200 cm$^{-1}$, ±50 wavenumbers, and another multiplet of peaks between about 1600 and about 600 cm$^{-1}$, ±50 wavenumbers, and an essential absence of peaks between about 1800 and about 2200 cm$^{-1}$, ±50 wavenumbers.

In an exemplary embodiment, according to any of the above paragraphs, wherein the crystalline polymorph has a multiplet of peaks between about 2800 and about 3200 cm$^{-1}$, ±50 wavenumbers, ±45 wavenumbers, ±40 wavenumbers, ±35 wavenumbers, ±30 wavenumbers, ±25 wavenumbers, ±20 wavenumbers, ±15 wavenumbers, ±10 wavenumbers, and ±5 wavenumbers.

In an exemplary embodiment, according to any of the above paragraphs, wherein the crystalline polymorph has multiplet of peaks between about 1600 and about 600 cm$^{-1}$, ±50 wavenumbers, ±45 wavenumbers, ±40 wavenumbers, ±35 wavenumbers, ±30 wavenumbers, ±25 wavenumbers, ±20 wavenumbers, ±15 wavenumbers, ±10 wavenumbers, and ±5 wavenumbers.

In an exemplary embodiment, according to any of the above paragraphs, wherein the crystalline polymorph has an essential absence of peaks between about 1800 and about 2200 cm$^{-1}$, ±50 wavenumbers, ±45 wavenumbers, ±40 wavenumbers, ±35 wavenumbers, ±30 wavenumbers, ±25 wavenumbers, ±20 wavenumbers, ±15 wavenumbers, ±10 wavenumbers, and ±5 wavenumbers.

In an exemplary embodiment, the invention provides a pharmaceutical composition comprising: a) the crystalline polymorph according to any of the above paragraphs; and b) at least one excipient or carrier.

In an exemplary embodiment, the invention provides a method for treating a disease in an animal suffering from the disease, comprising: administering to the animal a therapeutically effective amount of the crystalline polymorph of any of the above paragraphs, wherein said disease is associated with a bacteria.

In an exemplary embodiment, according to the above paragraph, wherein the bacteria is a Gram negative bacteria.

In an exemplary embodiment, according to any of the above paragraphs, wherein the bacteria is selected from the group consisting of *Neisseria* species, *Escherichia* species, *Shigella* species, *Salmonella* species, *Yersinia* species, *Klebsiella* species, *Proteus* species, *Enterobacter* species, *Serratia* species, *Vibrio* species, *Campylobacter* species, *Helicobacter* species, *Pseudomonas* species, *Bacteroides* species, *Haemophilus* species, *Bordetella* species, *Legionella* species, *Francisella* species, *Brucella* species, *Pasteurella* species, *Gardnerella* species, *Spirochetes* species, *Chlamydia* species and *Rickettsiae* species.

In an exemplary embodiment, according to any of the above paragraphs, wherein the disease is selected from the group consisting of meningitis, gonorrhea, otitis, otitis extema, folliculitis, diarrhea, urinary tract infections, sepsis, HAP, bacteremia, endocarditis, gastroenteritis, Typhoid fever, supsis, endocarditis, sinusitis, bubonic plague, enteric fever, hospital-acquired infection, skin and skin-structure infection, pneumonia, cholera, chronic gastritis, osteomylitis, burn-wound infections, corneal infections, periodontal disease, aspriation pneumonia, piglottitis, septic arthritis, chancroid, vaginitis, whooping cough, pontiac fever, tularemia, brucellosis, syphilis, Lyme disease, chlamydia, Rocky Mountain spotted fever, typhus, tracheobronchitis, walking pneumonia, urethritis, pyelonenephritis, intra-abdominal infection, febrile neutropenia, pelvic infection, bacteraemia, and septicaemia.

In an exemplary embodiment, according to any of the above paragraphs, wherein the disease is pneumonia.

In an exemplary embodiment, the invention is crystalline (S)-3-aminomethyl-7-(3-hydroxy-propoxy)-3H-benzo[c][1,2]oxaborol-1-ol.HCl, form HCl4.

In an exemplary embodiment, the invention is crystalline (S)-3-aminomethyl-7-(3-hydroxy-propoxy)-3H-benzo[c][1,2]oxaborol-1-ol.HCl, form HCl3.

In an exemplary embodiment, the invention is crystalline (S)-3-aminomethyl-7-(3-hydroxy-propoxy)-3H-benzo[c][1,2]oxaborol-1-ol.HCl, form HCl2.

In an exemplary embodiment, the invention is crystalline (S)-3-aminomethyl-7-(3-hydroxy-propoxy)-3H-benzo[c][1,2]oxaborol-1-ol.HCl, form HCl1.

In an exemplary embodiment, the invention is a method of preparing crystalline (S)-3-aminomethyl-7-(3-hydroxy-propoxy)-3H-benzo[c][1,2]oxaborol-1-ol.HCl, form HCl4, HCl3, HCl2, HCl1 as described herein.

In an exemplary embodiment, the invention is a method of preparing crystalline (S)-3-aminomethyl-7-(3-hydroxy-propoxy)-3H-benzo[c][1,2]oxaborol-1-ol.HCl, form HCl4, HCl3, HCl2, HCl1 as described in any of the above paragraphs.

The invention is further illustrated by the Examples that follow. The Examples are not intended to define or limit the scope of the invention.

EXAMPLES

All solvents used were commercially available and were used without further purification. Reactions were typically run using anhydrous solvents under an inert atmosphere of $N_2$.

HPLC analyses were performed on a Water 600 Controller system with a Waters 717 Plus Autosampler and a Waters 2996 Photodiode Array Detector. The column used was an ACE $C_{18}$, 5 µm, 4.6×150 mm. A linear gradient was applied, starting at 95% A (A: 0.1% $H_3PO_4$ in water) and ending at 90% B (B: MeCN) over 6 min and then maintained at 90% B until the 10 min mark. The column was then re-equilibrated over 3 min to 95:5 with a total run time of 20 min. The column temperature was at rt with the flow rate of 1.0 mL/min. The Diode Array Detector was scanned from 200-400 nm. For high purity samples requiring baseline subtraction, a linear gradient was applied, starting at 99% A (A: 0.1% $H_3PO_4$ in water) and ending at 90% B (B: MeCN) over 15 min. The column was then re-equilibrated over 3 min to 99% A with a total run time of 23 min. The column temperature was at rt with the flow rate of 1.0 mL/min. The Diode Array Detector was scanned from 200-400 nm. A blank MeOH sample was run immediately prior to the sample of which purity was to be determined: this was then subtracted to obtain the baseline subtracted chromatogram.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), vanillin (generated by dissolving about 1 g vanillin in 100 mL 10% $H_2SO_4$), potassium permanganate (generated by dissolving 1.5 g $KMnO_4$ and 10 g $K_2CO_3$ in 1.25 mL NaOH and 200 mL $H_2O$), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL $H_2O$ and 50 mL conc $H_2SO_4$) to visualize the compound. Flash chromatography was preformed using typically 40-63 µm (230-400 mesh) silica gel from Silicycle following analogous techniques to those disclosed by Still et al. Typical solvents used for flash chromatography or thin layer chromatography (TLC) were mixtures of $CHCl_3$/MeOH, $CH_2Cl_2$/MeOH, EtOAc/MeOH and hexane/EtOAc. Reverse phase flash chromatography were performed on a Biotage® using a Biotage $C_{18}$ cartridges and a $H_2O$/MeOH gradient (typically eluting from 5% MeOH/$H_2O$ to 90% MeOH/$H_2O$).

Preparative chromatography was performed on either a Waters Prep LC 4000 System using a Waters 2487 Diode Array or on a Waters LC Module 1 plus. The column used were either a Waters×Terra Prep $C_{18}$, 5 µm, 30×100 mm, Phenomenex Luna $C_{18}$, 5 µm, 21.6×250 mm, or a Phenomenex Gemini $C_{18}$, 5 µm, 100×30 mm. Narrow gradients with MeCN/$H_2O$ (water containing either 0.1% TFA, 0.1% AcOH, 0.1% $HCO_2H$ or 0.1% $NH_4OAc$) were used to elute the compound at a flow rate of approximately 20 mL/min and a total run time between 20-30 min.

Starting materials used were either available from commercial sources or prepared according to literature procedures and had experimental data in accordance with those reported. 6-aminobenzo[c][1,2]oxaborol-1(3H)-ol (C50), for example, can be synthesized according to the methods described in U.S. patent application Ser. No. 12/142,692, as well as U.S. Pat. Pubs. US20060234981 and US20070155699.

Example 1

Synthesis of (S)-3-aminomethyl-7-(3-hydroxy-propoxy)-3H-benzo[c][1,2]oxaborol-1-ol and Hydrochloride Polymorphs Thereof Conversion of 1 to 3

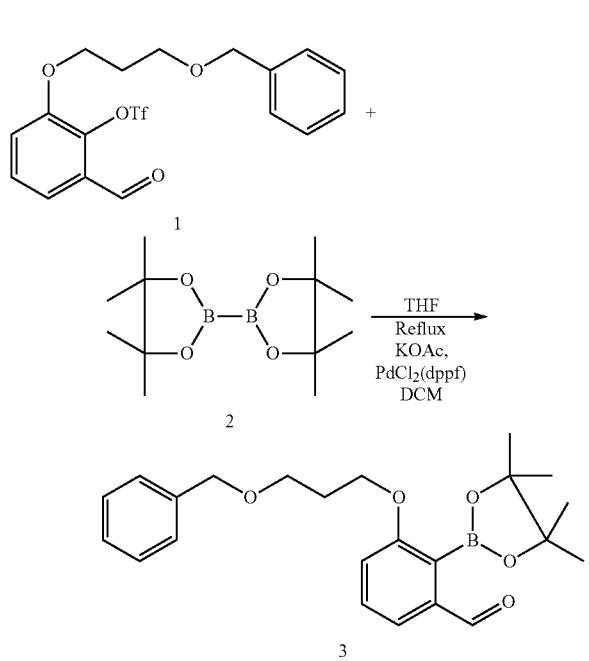

In a 22 L 3-neck round bottom flask under nitrogen was charged 870.0 g of 1, 636.0 g Bis (pinacolato) diboron 2, 415.0 g of KOAc, 94.0 g PdCl$_2$ (dppf).DCM, and 7.5 L THF. The resulting mixture was stirred, under nitrogen, for approximately 30 minutes. The mixture was heated to reflux from an initial temperature of 18° C. The reflux temperature (63° C.) was reached in 1 hr and 15 minutes. The mixture was left refluxing overnight. After approximately 15 hours of reflux, a sample of the mixture was removed and analyzed by HPLC to check for reaction completion. The reaction was not complete therefore refluxing was continued. After refluxing for approximately 4 more hours, reaction was complete by HPLC (≦1% 1).

The reaction mixture was allowed to cool to room temperature (T~25° C.) and 150 g of Celite was added. The mixture was stirred for approximately 1 hour. The reaction mixture was filtered on a ceramic funnel with filter paper. The solid was washed with 3×1 L THF (until the filtrate was clear and the solid was white or off white). The solid was mostly KOAc and other insoluble salt by-products formed during the reaction. The desired product was dissolved in the filtrate.

Using a Rotavap (bath temperature≦45° C.), the solvent was stripped from the filtrate until a thick dark oil remained.

The dark oil was redissolved in approximately 600 mL ethyl acetate. Celite (180 g) was added and the mixture stirred. To the stirring mixture, 8 L hexane was added via addition funnel over approximately 20-30 minutes. A black tar-like material precipitated and was adsorbed by the Celite enhancing filtration efficiency. The mixture was stirred over the weekend and then filtered on a funnel with GF paper. Solids were washed with 3×100 mL of 90/10 (vol/vol) hexane/ethyl acetate.

The filtrate was stripped to an oil using a Rotavap with the bath temperature kept to less than 40° C. Yield of 3: 960 g. HPLC purity was 76.8%.

Conversion of 3 to 5

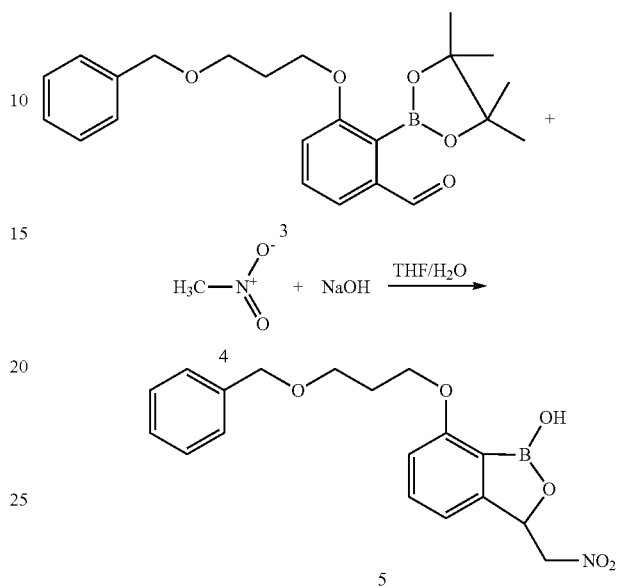

Procedure:

In a 22 L 3-neck round bottom flask was charged 86.0 g of NaOH and 2.75 L USP water. The solution was cooled to 10° C. or less in an ice bath. Nitro methane, 4, (384.0 g) was slowly added via addition funnel while maintaining a temperature of 15° C. or less. Addition of 4 took approximately 20 minutes. The resulting mixture was stirred for approximately 10 minutes. A solution of 3 (960 g) and 2.75 L THF was slowly added to the mixture via addition funnel Addition was done over approximately 1.5 hours. The temperature at the start of the addition was 8° C. and the temperature at the end of the addition was 10° C. When the addition was complete, the mixture was removed from the ice batch and allowed to warm to room temperature.

After stirring the reaction mixture for approximately 9 hours after the completion of the addition of the 3 starting material, HPLC showed that the reaction was complete (≦1% %5). The reaction mixture was cooled to 15° C. or less and quenched with 4.5 L USP water followed by 6 L MTBE. 2M HCl solution was added to the reaction mixture to adjust pH to pH~2 (pH adjustment required approximately 1200 mL 2M HCl solution). The reaction mixture was allowed to stand until the aqueous and organic layers separated. The organic layer was washed with 6×4 L USP water to remove the pinacol impurity. The organic layer was dried over approximately 500 g of sodium sulfate overnight. The mixture was filtered to remove the sodium sulfate and the solvent was removed resulting in an oil (Rotavap temperature≦40° C.). Yield of crude 5: 815 g. HPLC purity was 42.4%.

Crude material was chromatographed using a 6" glass column (GGC-5) packed with 10 kg silica gel in dichloromethane. The column was eluted with a solvent gradient: 100% dichloromethane (~40 L)→95:5 dichloromethane/MTBE (65 L). The "good" fractions were collected and the solvent removed to produce an oil (Rotavap temperature≦40° C.) to yield 710 g of amber oil. HPLC purity was 55.8%. The crude oil was dissolved in 500 mL MTBE. Hexane (500 mL) was added to the solution and the solution was stirred at room temperature for 2 days. The product precipitated out of solution and then was filtered and washed with 50:50 MTBE/hexane (3×200 mL). The product was dried in a vacuum oven at 40° C. Yield was 354 g. HPLC purity was 69%.

To upgrade purity, 354 g was recrystallized from MTBE. The yield of 5, first crop was 176 g of yellow solid. HPLC purity was 98.6%. A second crop of the material was isolated from the mother liquors. Approximately 460 g of mother liquors was loaded on a 6" glass column packed with 10 kg silica gel in dichloromethane. The column was eluted with: 100% dichloromethane (~60 L)→97.5:2.5 dichloromethane/ MTBE (60 L). The "good" fractions were collected and the solvent removed to produce an oil/solid. The solids were reslurried in hexane, filtered, and washed with hexane. The product was vacuum dried at 40° C. Yield of 5, second crop was 155.6 g. HPLC purity was 95.2%.

Hydrogenation of 5 to Produce 7

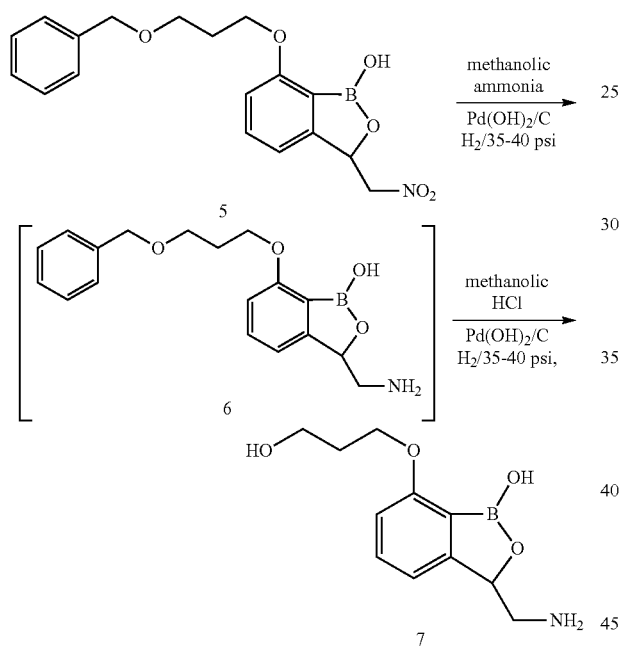

The following was charged to a 25 gal Reactor (Reactor R-21): 331 g of 5, 144 g 20% Pd(OH)$_2$/C, and 20 L of 2M NH$_3$/methanol solution. The volume of solvent for this reaction was based on the minimum stirring volume in the 25 gallon reactor. The reactor was pressurized and purged with nitrogen three times. The mixture was hydrogenated at 35-40 psi H$_2$ while circulating cold water through reactor jacket. The reaction was complete by HPLC analysis after approximately 17 hours. The reaction mixture was filtered through a cartridge (2 micron) into R-20 (second 25 gal glass lined reactor). R-21 was then rinsed with approximately 5 L methanol and the rinse transferred through a filter cartridge to R-20. The mixture was stripped mixture to an oil under vacuum (temperature≦40° C.). The residue was titrated with 3×10 L MTBE and stripped to an oil each time to remove excess NH$_3$. The oil was redissolved in ~0.65M HCl/methanol solution. The solution was transferred back to R-21 and the reactor was charged with 72 g 20% Pd(OH)$_2$/C catalyst. The reactor was purged three times with nitrogen. The mixture was hydrogenated at 35-40 psi H$_2$ while circulating cold water through the reactor jacket. The reaction was complete by HPLC analysis after approximately 3 hours. The reaction mixture was filtered through a cartridge (2 micron) into R-20. R-21 was rinsed with approximately 5 L methanol and the rinsed methanol was sent through a filter cartridge into R-20. Samples were submitted for % Pd at various points throughout the process to pinpoint the effectiveness of the Pd removal and to make sure the batch would pass the % Pd specification. The filtered solution was treated with 25 g of thiol silica and stirred at room temperature overnight. The mixture was filtered through a 2 micron filter cartridge into 20 L glass carboys.

The filtered solution was stripped to an oil using a Rotavap (temperature≦40° C.). Crystals started forming while stripping. Methanol (300 mL) was added to the oil and the mixture stirred at room temperature overnight. A thick slurry of crystallized product was obtained. Approximately 2 L of MTBE was added to the slurry and the mixture was cooled to about 10-15° C. for approximately 2 hours. The solid was filtered and washed with 3×750 mL MTBE and pulled dry until the material was collected and placed on trays. The solid was vacuum dried at T=40° C. The amount of first crop was 174.0 g. HPLC Purity was 97.9%.

A second crop of crystals was obtained from mother liquors. Yield of second crop was 23.8 g. HPLC Purity was 87.9%.

Isolation of the S Isomer of 7 by Crystallization of 10

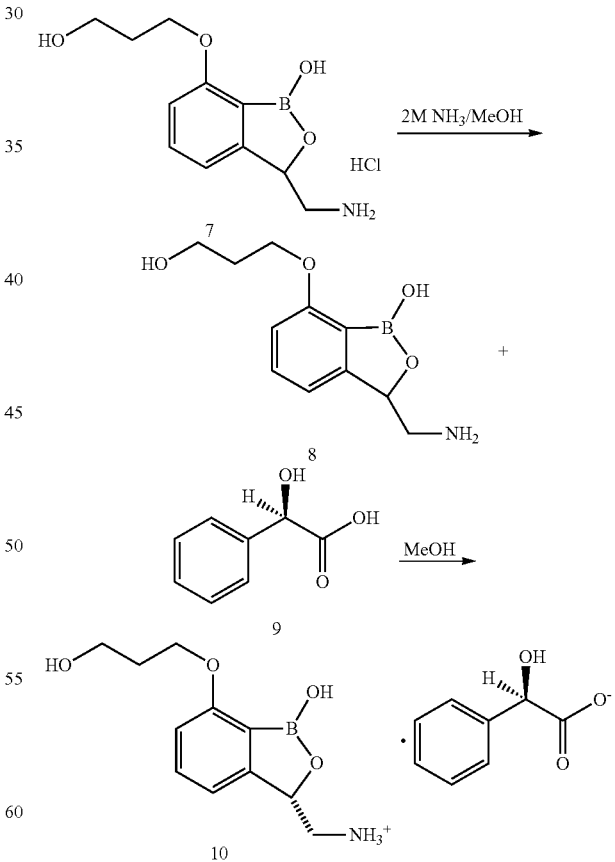

Procedure:

In a 5 L 3-neck round bottom flask was dissolved 196.3 g of racemic 7 HCl in sufficient methanol to effect complete dissolution (approximately 2.5 L). The solution was stirred and thiol silica (24 g) was added. Stirring at room temperature continued for approximately 3 hours. The mixture was filtered through GF paper to remove the silica. The silica was washed twice with 100 mL MeOH. The solution was sampled for % Pd. The filtered solution was cooled to approximately 10-15° C. 2M NH$_3$/methanol solution (740 mL) was slowly added while maintaining the temperature at ≦25° C. The pH of the final mixture was approximately 12 (litmus paper). The solution was stripped to a thick slurry via Rotavap (temperature≦40° C.). The stripped residue was titrated with 3×400 mL Ethanol SDA-3A to remove excess NH$_3$. The solution was stripped to a thick slurry after each addition of ethanol. EtOH SDA-3A (1200 ml) was added to the resulting slurry and stirred for approximately 30 minutes. An additional 1500 mL methanol was added to the mixture. The solution stirred for 30 minutes. The mixture was filtered through GF paper to remove insoluble salts and then washed with 3×300 mL MeOH. Salts were collected and dried for mass balance (approximately 64.2 g). The clear filtrate was stripped to a solid/slurry Rotavap (temperature≦40° C.). The stripped 7 free-base was dissolved in 1850 mL methanol. A clear solution was obtained.

A solution of 108.8 g R-(−)-Mandelic Acid in 400 ml methanol was added to the 7 freebase solution. The temperature was approximately 25° C. The resulting solution was allowed to crystallize overnight. To increase the yield of 10, the mixture was allowed to settle and the clear solution was transferred to a Rotavap flask and stripped to approximately one-half of the original volume. The stripped solution was transferred back to the original flask holding the settled crystals and the mixture was allowed to stir at room temperature overnight. The solution was filtered and washed with 3×300 mL methanol then vacuum dried at 40° C. Yield of 10: 40.0 g. HPLC Purity was 99.7%.

A second crop of 18.0 g and a third crop of 51.9 g were obtained.
Conversion of 10 to 11:
Preparation of the HCl1 Form

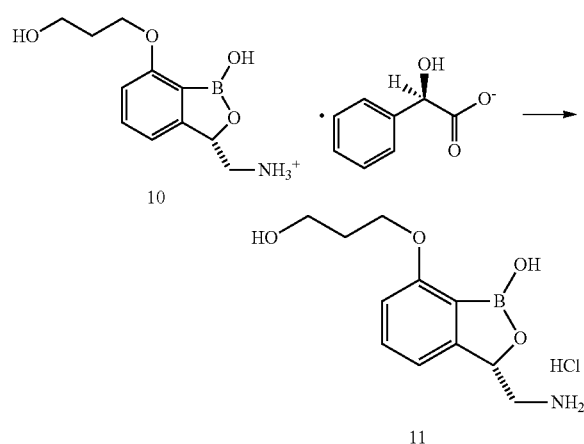

Procedure:

To a 1000 mL round bottom flask was charged 500 mL of 1M HCl solution and 39.6 g 10. The mixture was stirred for approximately 5 minutes and then 350 ml of MTBE was added. The resulting mixture was vigorously stirred until all solid dissolved and a biphasic mixture resulted. The mixture was filtered through GF paper to remove insoluble particles. The layers were allowed to split on a separatory funnel and the organic layer was discarded. The aqueous layer was washed with 5×350 mL MTBE to remove all the mandelic acid. The organic layers were discarded. A sample of the aqueous layer was checked by HPLC to verify removal of mandelic acid. The aqueous layer was placed in the Freeze Dryer (FD-1 Virtis Freezemobile 25ES). The initial temperature was 19° C. After approximately 2 hours, the product was frozen and temperature was approximately −45° C. The shelf temperature was increased to −20° C. After approximately 3 days, the shelf temperature was raised to 0° C. After 4 hours, the shelf temperature was raised to 20° C. After an additional 4.5 hours, the shelf temperature was increased to 30° C. After approximately 16.5 hours at the shelf temperature of 30° C., the product was taken out of the freeze dryer and packaged in Nalgene bottles. Yield of 11: 28.5 g.

Process of the Preparation of the Free Base of (S)-3-aminomethyl-7-(3-hydroxy-propoxy)-3H-benzo[c][1,2]oxaborol-1-ol 35.05 g of Amberlyst A26 OH resin (exchange capacity: 4.4 meq./g compound) was added to 175 mL methanol/water (95/5, v/v), and left overnight. The resin was then recovered by filtration and washed with 175 mL methanol/water (95/5, v/v).

An amount of 3.9 g (14.28 mmol) of the hydrochloride salt of (S)-3-aminomethyl-7-(3-hydroxy-propoxy)-3H-benzo[c][1,2]oxaborol-1-ol was dissolved in 70 mL methanol/water (95/5, v/v). This solution was put in contact with 39 g of the resin. The HCl salt and the resin were left in contact for 1 hour in order to make the exchange, after which the resin was filtered off.

The free base of (S)-3-aminomethyl-7-(3-hydroxy-propoxy)-3H-benzo[c][1,2]oxaborol-1-ol was isolated as a solid from the above resulting solution by evaporation, under vacuum at room temperature (RT) using a rotary-evaporator.

Example 2

Process of the (S)-3-aminomethyl-7-(3-hydroxy-propoxy)-3H-benzo[c][1,2]oxaborol-1-ol.HCl Salt Form Preparation Preparation of the HCl2 Form Approximately 4 mg of the free base (S)-3-aminomethyl-7-(3-hydroxy-propoxy)-3H-benzo[c][1,2]oxaborol-1-ol was dissolved in 0.4 mL methanol/water (95/5, v/v). An aqueous solution of hydrochloric acid (37% conc.) was added such that the molar ratio of (S)-3-aminomethyl-7-(3-hydroxy-propoxy)-3H-benzo[c][1,2]oxaborol-1-ol to the hydrochloric acid was 1:1.1. The solution was then warmed up (10° C./min) to 60° C. and kept at 60° C. for 1 hour. Afterwards the solution was cooled down with 20° C./h to 5° C. and then aged for 48 h at 5° C. The solvent was then evaporated under vacuum (17.5 hours at 500 mbar followed by 72 hours at 200 mbar) at room temperature, until dryness.

Recrystallization of the HCl2 Form

The HCl2 form was also obtained by re-crystallization from ethanol/water (95/5, v/v) of the HCl2 form. In this process an amount of approximately 4 mg of HCl2 salt form was dissolved in approximately 1 mL of ethanol/water (95/5, v/v). The solution was then warmed up (10° C./min) to 60° C. and kept at 60° C. for 1 hour. Afterwards the solution was cooled down with 20° C./h to 5° C. and then aged for 48 h at 5° C. The solvent was then evaporated under vacuum (17.5 hours at 500 mbar followed by 72 hours at 200 mbar) at room temperature, until dryness.

Preparation of the HCl3 Form

Approximately 4 mg of the HCl2 form of (S)-3-aminomethyl-7-(3-hydroxy-propoxy)-3H-benzo[c][1,2]oxaborol-1-ol was dissolved in 0.4 mL pentane. The solution was then warmed up (10° C./min) to 60° C. and kept at 60° C. for 1 hour. Afterwards the solution was cooled down with 20° C./h to 5° C. and then aged for 48 h at 5° C. The solvent was then evaporated under vacuum (17.5 hours at 500 mbar followed by 72 hours at 200 mbar) at room temperature, until dryness.

Alternate Preparation of the HCl3 Form

Approximately 4 mg of the HCl2 form of (S)-3-aminomethyl-7-(3-hydroxy-propoxy)-3H-benzo[c][1,2]oxaborol-1-ol was dissolved in 0.4 mL tetrahydrofuran. The solution was then warmed up (10° C./min) to 60° C. and kept at 60° C. for 1 hour. Afterwards the solution was cooled down with 20° C./h to 5° C. and then aged for 48 h at 5° C. The solvent was then evaporated under vacuum (17.5 hours at 500 mbar followed by 72 hours at 200 mbar) at room temperature, until dryness.

Alternate Preparation of the HCl3 Form

Approximately 4 mg of the HCl2 form of (S)-3-aminomethyl-7-(3-hydroxy-propoxy)-3H-benzo[c][1,2]oxaborol-1-ol was dissolved in 0.4 mL acetone. The solution was then warmed up (10° C./min) to 60° C. and kept at 60° C. for 1 hour. Afterwards the solution was cooled down with 20° C./h to 5° C. and then aged for 48 h at 5° C. The solvent was then evaporated under vacuum (17.5 hours at 500 mbar followed by 72 hours at 200 mbar) at room temperature, until dryness.

Preparation of the HCl4 Form—Method A

Approximately 59 mg of the free base (S)-3-aminomethyl-7-(3-hydroxy-propoxy)-3H-benzo[c][1,2]oxaborol-1-ol was dissolved in 2.5 mL methanol/water (95/5, v/v). An aqueous solution of hydrochloric acid (37% conc.) was added such that the molar ratio of (S)-3-aminomethyl-7-(3-hydroxy-propoxy)-3H-benzo[c][1,2]oxaborol-1-ol to the hydrochloric acid was 1:1.1. The system was then warmed up (10° C./min) to 60° C. and kept at 60° C. for 1 hour. After this the system was cooled down with 20° C./h to 5° C. and then aged for 48 h at 5° C. The solvent was then evaporated under vacuum (66.5 hours at 200 mbar followed by 7.3 hours at 1 mbar) at room temperature, until dryness.

Recrystallization of the HCl4 Form—Method A

The HCl4 form was also obtained by re-crystallization from pentane of the HCl4 form. In this process an amount of approximately 59 mg of HCl4 salt form was dissolved in approximately 2.5 mL of pentane. The solution was then warmed up (10° C./min) to 60° C. and kept at 60° C. for 1 hour. Afterwards the solution was cooled down with 20° C./h to 5° C. and then aged for 48 h at 5° C. The solvent was then evaporated under vacuum (66.5 hours at 200 mbar followed by 7.3 hours at 1 mbar) at room temperature, until dryness.

Preparation of the HCl4 Form—Method B

Isopropanol (50.3 kg) was charged into a clean reactor with freeze-dried (S)-3-aminomethyl-7-(3-hydroxy-propoxy)-3H-benzo[c][1,2]oxaborol-1-ol (2.37 kg). The mixture was heated to reflux (~82° C.), and the reactor was charged with water (5.85 kg) over the course of 30 mins. The reaction mixture was stirred at reflux for 55 mins, and a second aliquot of water was charged into the reactor (0.5 kg) to produce a clear solution. The hot solution was filtered through a 0.2 micron cartridge filter into a second reactor. The filtered solution was heated to reflux, and the solution was reduced to 25% of its original volume by atmospheric distillation. Heating was ceased, and the mixture was allowed to cool naturally to 25° C. and after which time it was stirred for 12 hours. The product was isolated by funnel filtration, washed with isopropanol (3.5 kg), and dried for 22 hours via a shelf dryer at 40° C. with at least 26 inches of vacuum.

Example 3

Stability Study

The HCl1 polymorph, which was a hard bulky material, was placed in a closed Amber bottle and stored under ambient conditions. Four months later, the bottle was opened, and the hard bulky material was now a free flowing powder. An XRPD was taken of this free flowing powder. The similarities in the XRPD of the free flowing powder with a reference XRPD of the HCl4 form indicates that the free flowing powder is in the HCl4 form. The result indicates that the initial HCl1 form had converted into the HCl4 form during storage. This result indicates that HCl4 is a more stable polymorph than HCl1. XRPD data comparing the free base form, polymorph form HCl1 and polymorph form HCl4 is provided in FIG. 5.

Example 4

Alternative methods for preparing polymorph form HCl1, form HCl2, form HCl4, and form HCl5 involve the use of a form screen procedure. The input material for the screen was a nonsolvated form of the hydrochloride salt of (S)-3-aminomethyl-7-(3-hydroxy-propoxy)-3H-benzo[c][1,2]oxaborol-1-ol. This was the predominant form produced within the screen and is the most stable form at room temperature. Screening was conducted in a total of 48 solvents/solvent mixtures using four different crystallization modes listed below. The solvents included water, methanol, 1-propanol, nitromethane, acetonitrile, dimethylsulfoxide, acetone, 2-butanone, dichloromethane, methyl acetate, 4-methyl-2-chloroform, ethyl acetate, chlorobenzene, tetrahydrofuran, 1,4-dioxane, isopropyl ether, toluene, cyclohexane, heptanes, 1-butanol, 2-propanol, trifluoroethanol, dimethyl carbonate, t-butyl methyl ether, isopropyl acetate, ethanol, 1-methoxy-2-propanol, cyclohexanone, dimethyl formamide, 2-methoxyethyl ether, methanol:5 vol % $H_2O$, acetonitrile:5 vol % $H_2O$, acetone:5 vol % $H_2O$, tetrahydrofuran:5 vol % $H_2O$, 2-propanol:5 vol % $H_2O$, methanol:10 vol % $H_2O$, acetonitrile:10 vol % $H_2O$, acetone:10 vol % $H_2O$, tetrahydrofuran:10 vol % $H_2O$, dioxane:10 vol % $H_2O$, 2-propanol:10 vol % $H_2O$, isopropanol+10% dimethylsulfoxide, acetonitrile+10% dimethylsulfoxide, and n-methylpyrrolidone.

Vapor diffusions were also conducted in selected solvents. The four crystallization modes used were:
  temperature-cycled ripening of slurries
  rapid cooling of room-temperature solutions
  room-temperature evaporation of solutions
  vapor diffusion of solvent/anti-solvent combinations Characterization:

All samples from the screen were isolated and analyzed by Raman spectroscopy. The samples were then grouped based on Raman spectral match. Representative samples from each of the groups were further analyzed by additional analytical techniques as appropriate (XPRD, DSC, TG-IR, PLM, etc.).

Screen Results

The temperature-cycle, rapid cool, and vapor diffusion samples formed a single group (Group A/Input) based on Raman and XPRD analyses. Most evaporative samples also produced Group A. However, five additional groups (Group B, Group C, Group D, Group E, and Group F) were produced from evaporative and evaporative scale-up experiments based on Raman analyses. These groups were selected for further analysis and/or scale-up.

Group B was an evaporative experiment from nitromethane produced in very low yields (<3 mg). This sample was analyzed by Raman, XPRD, and DSC. Insufficient sample was present for TG-IR (thermogravimetric-infrared spectroscopy). Six scale-up experiments were set up and each produced an amorphous or oily solid. The XPRD data did not match any of the known forms, and an unusually large low angle peak was present. The remaining seeds were used in a competitive ripening experiment in nitromethane with the input. Raman analysis after one week matched Group A (polymorph form HCl4).

Group C was produced from two evaporative experiments from acetone and 2-butanone in very low yields (<1 mg). This sample was analyzed by Raman, and insufficient sample was present for further analysis. A total of fourteen scale-up experiments were set up, seven in acetone and seven in 2-butanone. The acetone experiments resulted in either Group A (polymorph form HCl4) or amorphous/oily solids. Most of the 2-butanone experiments produced a new group, Group E. Since scale-up experiments for Group C were unsuccessful, the remaining seeds were used in a competitive ripening experiment in acetone with the input. Raman analysis after one week matched Group A, polymorph form HCl4.

Group D, a newly identified polymorph referred to as polymorph form HCl5, was produced from a very slow evaporation experiment from acetone with 20% water in good yields (~20 mg). This sample was analyzed by Raman and was unstable and converted to Group E (polymorph form HCl3).

Group E was analyzed by Raman, XPRD, DSC, and TG-IR. Loss of 6.4% water (1.0 eq) was initially seen by TG-IR, and after one week, a repeat TG experiment showed loss of 4.9% water (0.8 eq). Three attempts to reproduce the Group D/E form in acetone/water mixtures were unsuccessful and resulted in Group A (polymorph form HCl4).

Group F was produced from several evaporative scale-up experiments in 2-butanone in very low yields (<0.5 mg). This sample was analyzed by Raman, XPRD, and DSC. Insufficient sample was present for TG-IR. However, closer analysis of the Raman, XPRD, and DSC data strongly suggests that Group F is a mixture of Group A (polymorph form HCl4) and E (polymorph form HCl3).

Single crystal data confirms that the HCl4 polymorph is nonsolvated and crystallizes as the non-cyclized structure shown below.

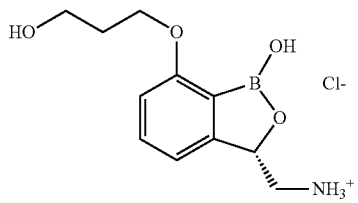 [SMILES: [NH3+]C[C@H]1OB(O)c2c(OCCCO)cccc21 ; [Cl-]]

Example 5

X-ray Powder Diffraction (XRPD) Collection Information

XRPD patterns were obtained using a high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings.

Data collection was carried out at room temperature using monochromatic $CuK_\alpha$ radiation in the 2θ region between 1.5° and 41.5°. The diffraction pattern of each well was collected with an exposure time of 90 s for each frame. No background subtraction or curve smoothing was applied to the XRPD patterns.

The carrier material used during XRPD analysis was transparent to X-rays and contributed only slightly to the background.

Example 6

Single Crystal X-Ray

Two samples of the hydrochloride salt of (S)-3-aminomethyl-7-(3-hydroxy-propoxy)-3H-benzo[c][1,2]oxaborol-1-ol were submitted for single crystal structure analysis. Preliminary examination and data collection were performed with Cu $K_\alpha$ radiation (λ=1.54184 Å) on a Rigaku Rapid II equipped with confocal optics. Refinements were performed on an LINUX PC using SHELX97 (Sheldrick, G. M. *Acta Cryst.*, 2008, A64, 112).

Cell constants and an orientation matrix for data collection were obtained from least-squares refinement using the setting angles of 9176 reflections in the range 7°<θ<66° [Crystal-Clear: *An Integrated Program for the Collection and Processing of Area Detector Data*, Rigaku Corporation, © 1997-2002]. The space group was determined by the program XPREP [Bruker, XPREP in SHELXTL v. 6.12, Bruker AXS Inc., Madison, Wis., USA, 2002].

Structure Solution and Refinement

The structure was solved by direct methods using Charge Flipping [Oszlanyi G., Suto, A. *Acta Cryst*, 2004, A60, 134] algorithm in PLATON [Spek, A. L. *PLATON. Molecular Graphics Program*. Utrecht University, Utrecht, The Netherlands, 2008. Spek, A. L, *J. Appl. Cryst.* 2003, 36, 7].

Scattering factors were taken from the "International Tables for Crystallography" [International Tables for Crystallography, Vol. C, Kluwer Academic Publishers: Dordrecht, The Netherlands, 1992, Tables 4.2.6.8 and 6.1.1.4].

Results and Discussion

The orthorhombic cell parameters and calculated volume are: a=9.1045(2) Å, b=10.3107(2) Å, c=14.5988(3) Å, α=90.00°, β=90.00°, γ=90.00°, V=1370.44(5) Å$^3$. The formula weight of the asymmetric unit in the crystal structure of the hydrochloride salt of (S)-3-aminomethyl-7-(3-hydroxy-propoxy)-3H-benzo[c][1,2]oxaborol-1-ol is 273.53 amu·(asymmetric unit)$^{-1}$ with Z=4, resulting in a calculated density of 1.326 g cm$^{-3}$. The space group was determined to be P2$_1$2$_1$2$_1$. The quality of the structure obtained was high, as indicated by the R-value of 0.027 (2.7%). Usually R-values in the range of 0.02 to 0.06 are quoted for the most reliably determined structures [Glusker, Jenny Pickworth; Trueblood, Kenneth N. *Crystal Structure Analysis: A Primer*, 2$^{nd}$ ed.; Oxford University press: New York, 1985; p. 87].

Crystal Data and Data Collection Parameters for the hydrochloride salt of (S)-3-aminomethyl-7-(3-hydroxy-propoxy)-3H-benzo[c][1,2]oxaborol-1-ol are provided in the X-Ray Single Crystal Table below:

| | |
|---|---|
| formula | $C_{11}H_{17}BClNO_4$ |
| formula weight | 273.53 |
| space group | $P2_12_12_1$ (No. 19) |
| a, Å | 9.1045(2) |
| b, Å | 10.3107(2) |
| c, Å | 14.5988(3) |
| V, Å$^3$ | 1370.44(5) |
| Z | 4 |
| $d_{calc}$, g cm$^{-3}$ | 1.326 |
| crystal dimensions, mm | 0.22 × 0.14 × 0.12 |
| temperature, K | 150. |
| radiation (wavelength, Å) | Cu K$_a$ (1.54184) |
| monochromator | graphite |
| linear abs coef, mm$^{-1}$ | 2.552 |
| absorption correction applied | empirical[a] |
| transmission factors: min, max | 0.481, 0.736 |
| diffractometer | Nonius KappaCCD |
| h, k, l range | −10 to 10 −12 to 12 −17 to 16 |
| 2θ range, deg | 14.33-133.20 |
| mosaicity, deg | 1.25 |
| programs used | SHELXTL |
| $F_{000}$ | 576.0 |
| weighting $1/[\sigma^2(F_o^2) + (0.0405P)^2 + 0.0000P]$ where $P = (F_o^2 + 2F_c^2)/3$ | |
| data collected | 9176 |
| unique data | 2305 |
| $R_{int}$ | 0.054 |
| data used in refinement | 2305 |
| cutoff used in R-factor calculations | $F_o^2 > 2.0\sigma(F_o^2)$ |
| data with I > 2.0σ(I) | 2233 |
| number of variables | 183 |
| largest shift/esd in final cycle | 0.00 |
| R(F$_o$) | 0.027 |
| R$_w$(F$_o^2$) | 0.072 |
| goodness of fit | 1.090 |
| absolute structure determination | Flack parameter[b] (0.009(12)) Hooft parameter[c] (0.012(8)) Friedel coverage 92% |

[a]CrystalClear: An Integrated Program for the Collection and Processing of Area Detector Data, Rigaku Corporation, © 1997-2002.
[b]Flack, H. D. Acta Ctyst., 1983 A39, 876.
[c]Hooft, R. W. W., Straver, L. H., and Spek, A. L. J. Appl. Ctyst., 2008, 41, 96.

Example 7

X-Ray Powder Diffraction (XRPD) of Single Crystal Samples

X-ray powder diffraction (XRPD) analyses were performed on the X-ray single crystal samples described in Example 6. X-ray powder diffraction (XRPD) analyses used an Inel XRG-3000 diffractometer equipped with a CPS (Curved Position Sensitive) detector with a 2θ range of 120°. Real time data were collected using Cu—Kα radiation starting at approximately 4° 2θ at a resolution of 0.03° 2θ. The tube voltage and amperage were set to 40 kV and 30 mA, respectively. The monochromator slit was set at 5 mm by 160 μm. The pattern is displayed from 2.5-40°2θ. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard. The experimental XRPD pattern was collected at SSCI, Inc. according to cGMP specifications.
Form HCl4
FIGS. 7 and 8A show two different experimental XRPD pattern collected for two different preparations of the hydrochloride salt of (S)-3-aminomethyl-7-(3-hydroxy-propoxy)-3H-benzo[c][1,2]oxaborol-1-ol.
FIG. 7 is an XRPD pattern collected from a sample of polymorph form HCl4 prepared according to Example 2, Method A.

The X-ray powder diffraction pattern shown in FIG. 8A was obtained using a sample of polymorph form HCl4 prepared as described in Example 2, Method B, and was acquired using a PANalytical X'Pert Pro diffractometer. Samples were gently flattened onto a zero-background silicon insert sample holder. A continuous 2θ scan range of 2 to 40 degrees was used with a CuKα radiation source and a generator power of 40 kV and 45 mA. A 2θ step size of 0.017 degrees/step with a step time of 20.0 seconds was used. Samples were rotated at 30 rpm. Experiments were performed at room temperature and at ambient humidity. FIG. 8B lists peaks at degrees 2θ±0.2 degrees 2θ and d-spacing values which characterize (S)-3-aminomethyl-7-(3-hydroxy-propoxy)-3H-benzo[c][1,2]oxaborol-1-ol polymorph form HCl4 as shown in FIG. 8A. In exemplary embodiments, the entire list of peaks, or a subset thereof, may be sufficient to characterize (S)-3-aminomethyl-7-(3-hydroxy-propoxy)-3H-benzo[c][1,2]oxaborol-1-ol polymorph form HCl4.

Example 8

Differential Scanning Calorimetry

Figure 9:
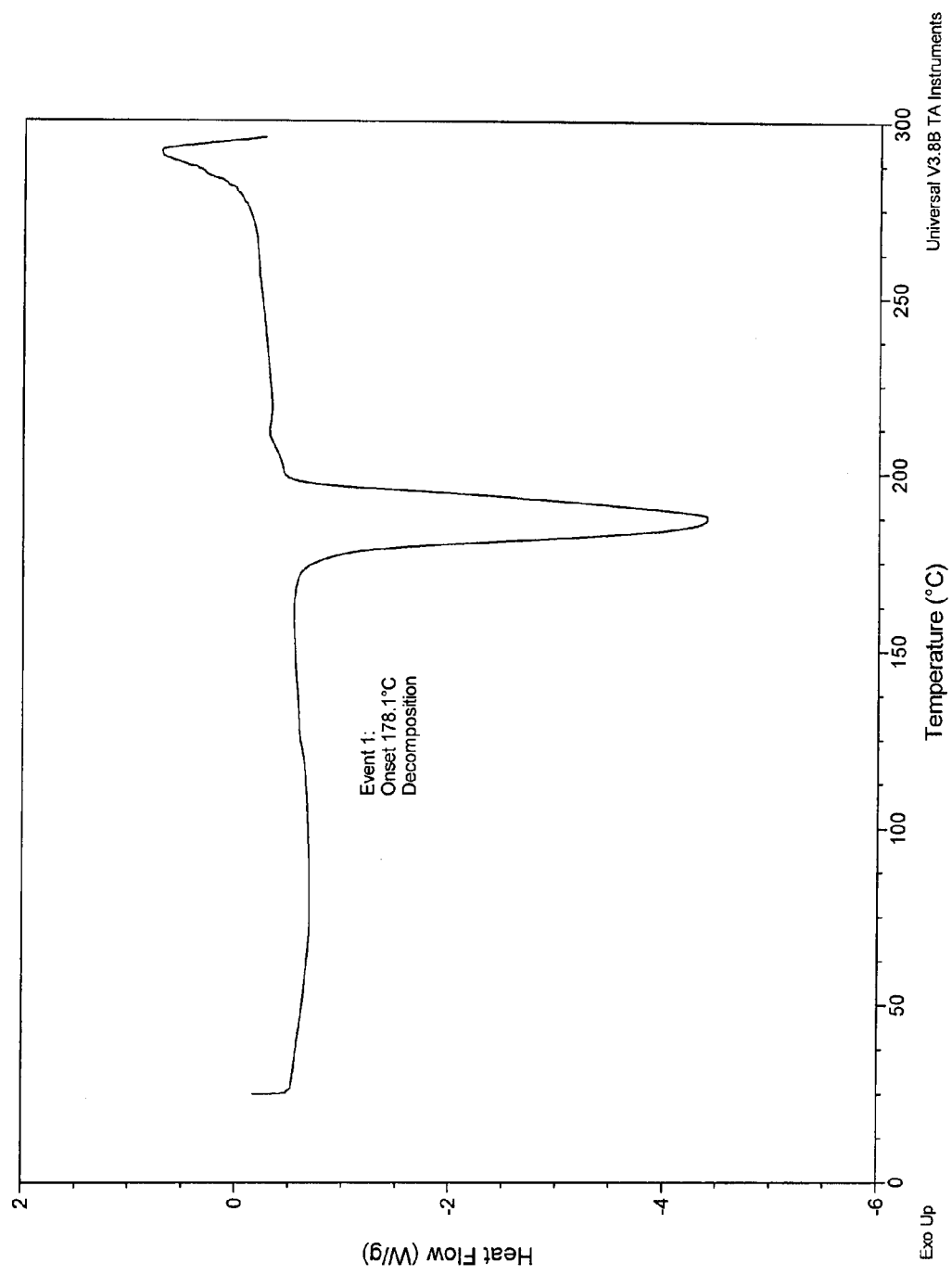
FIG. 9 is a differential scanning calorimetry (DCS) thermogram of the hydrochloride salt of (S)-3-aminomethyl-7-(3-hydroxy-propoxy)-3H-benzo[c][1,2]oxaborol-1-ol referred to as polymorph form HCl4.
Figure 10:
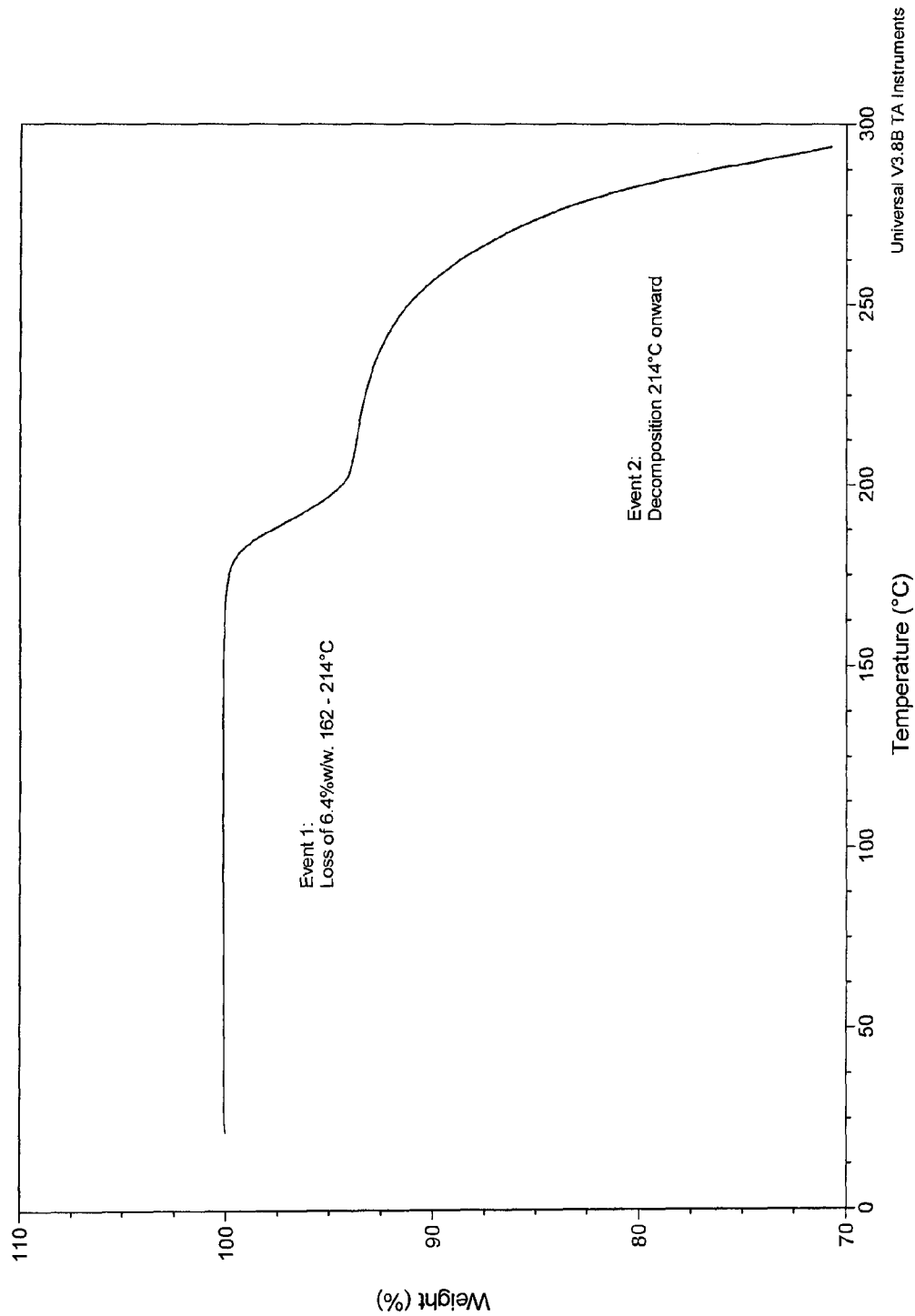
FIG. 10 is a thermogravimetric analyzer (TGA) thermogram of the hydrochloride salt of (S)-3-aminomethyl-7-(3-hydroxy-propoxy)-3H-benzo[c][1,2]oxaborol-1-ol referred to as polymorph form HCl4.

Instrument: TA Instruments Thermal Analysis System, Model DSC Q100
Key Operating Parameters:
Module—DSC Standard Cell FC
Method—Ramp
Pan: Closed aluminum
Purge gas: N$_2$, 40 mL/min
Cell# FC-00615
Method 1: Equilibrate at 25.00° C.
Method 2: Ramp 15.00° C./min to 300.00° C.
Form HCl4
FIG. 9 shows a DSC thermogram for a sample of the hydrochloride salt of (S)-3-aminomethyl-7-(3-hydroxy-propoxy)-3H-benzo[c][1,2]oxaborol-1-ol.
The DSC thermogram was acquired using a TA Instruments Q100 Differential Scanning calorimeter, as indicated above. A sample of (S)-3-aminomethyl-7-(3-hydroxy-propoxy)-3H-benzo[c][1,2]oxaborol-1-ol polymorph form HCl4 prepared in Example 2, Method B, was accurately weighed out directly into an aluminum DSC pan. The pan was sealed by applying pressure by hand and pushing each part of the pan together (also known as a loose lid configuration). The temperature was ramped at a rate of 15° C./minute. An endothermic transition having an onset of 178.1° C. was measured, and is associated with a decomposition event.
FIG. 10 shows a TGA thermogram acquired using a TA Instruments Q500 Thermogravimetric Analyzer. The sample pan was tared, and sample of (S)-3-aminomethyl-7-(3-hydroxy-propoxy)-3H-benzo[c][1,2]oxaborol-1-ol polymorph form HCl4 prepared in Example 2, Method-B, was placed in the pan. The temperature was ramped at a rate of 15° C./minute. A stepwise weight-loss of 6.4% was observed between 162 and 214° C. and is associated with water-loss due to reversible chemical transformation. Further decomposition is observed beyond 214° C.
Form HCl3
Form HCl3 exhibits characteristics consistent with a hydrated crystalline form in that it exhibits a weight loss below 100° C. that coincides with the evolution of water.
Method of Preparation:
A solution of isopropanol containing 20% water by volume was added to a vial containing approximately 25 mg of polymorph form HCl4. The resulting mixture was stirred as the temperature was cycled between 0 and 40° C. over the course of 48 hours. The solution was isolated by filtration and evaporated to dryness. The freshly isolated product was verified to be Form HCl5. Form HCl5 was stored in a sealed vial for at least 7 days which resulted in conversion to Form HCl3.

Figure 11:
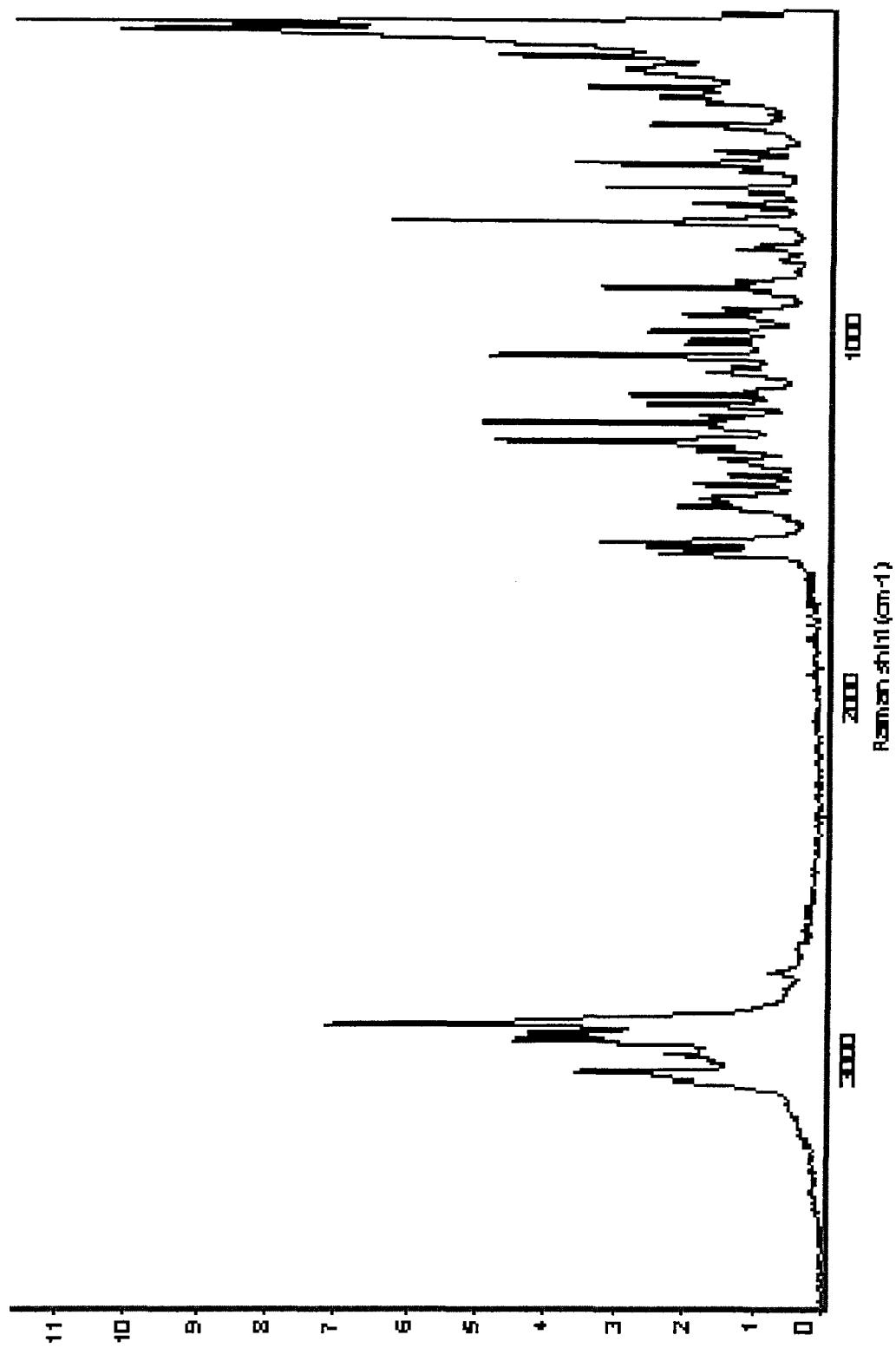
FIG. 11 is a Raman spectroscopy analysis of the hydrochloride salt of (S)-3-aminomethyl-7-(3-hydroxy-propoxy)-3H-benzo[c][1,2]oxaborol-1-ol referred to as polymorph form HCl3.

FIG. 11 shows a FT-Raman spectrum recorded on a Nicolet NXR 9650 FT-Raman Spectrometer at a resolution of 4 cm$^{-1}$ with excitation from a Nd:YVO4 laser ($\lambda$=1064 nm). Form HCl3 exhibits peaks at the following wavenumbers (cm$^{-1}$): 33049.9, 2962.2, 2941.8, 2918.2, 1583.3, 1297.9, 1247.4, 1066.5, 870.4, 686.1, 530.5, 316.2, 228.5, 161.4, 137.1. In exemplary embodiments, the entire list of peaks, or a subset thereof, may be sufficient to characterize (S)-3-aminomethyl-7-(3-hydroxy-propoxy)-3H-benzo[c][1,2]oxaborol-1-ol polymorph form HCl3.

Figure 12A:
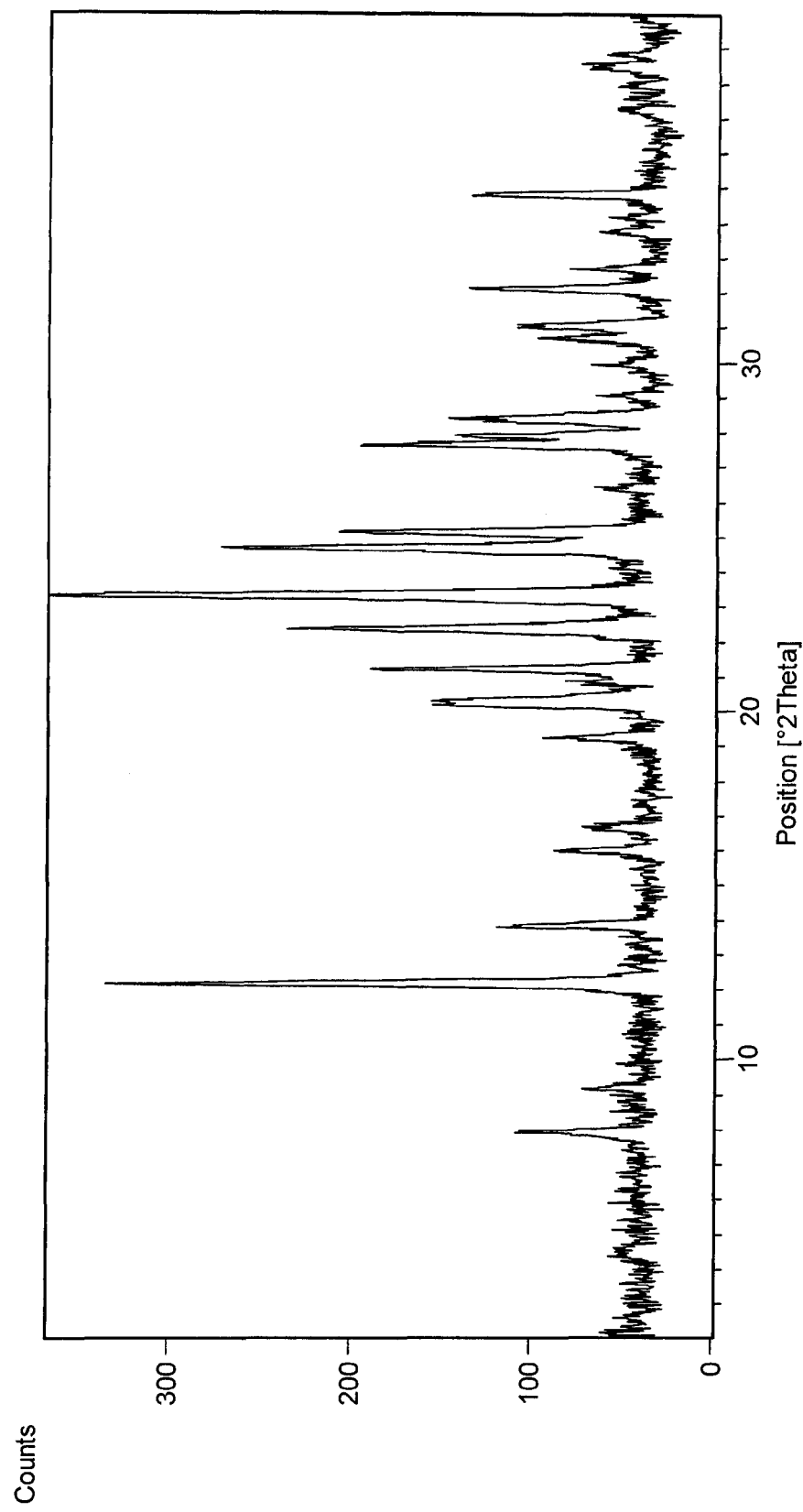
FIG. 12A is a second X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl3.

In addition, X-ray powder diffraction pattern of (S)-3-aminomethyl-7-(3-hydroxy-propoxy)-3H-benzo[c][1,2]oxaborol-1-ol polymorph form HCl3 prepared in Example 2 was acquired using a PANalytical X'Pert Pro diffractometer. Samples were gently flattened onto a zero-background silicon insert sample holder. A continuous 2θ scan range of 2 to 40 degrees was used with a CuKα radiation source and a generator power of 40 kV and 45 mA. A 2θ step size of 0.017 degrees/step with a step time of 20.0 seconds was used. Samples were rotated at 30 rpm. Experiments were performed at room temperature and at ambient humidity. FIG. 12B lists peaks at degrees 2θ±0.2 degrees 2θ, and d-spacing values (in angstroms), which characterize Form HCl3 as seen in the XRPD pattern of FIG. 12A. In exemplary embodiments, the entire list of peaks, or a subset thereof, may be sufficient to characterize (S)-3-aminomethyl-7-(3-hydroxy-propoxy)-3H-benzo[c][1,2]oxaborol-1-ol polymorph form HCl3.

Figure 13:
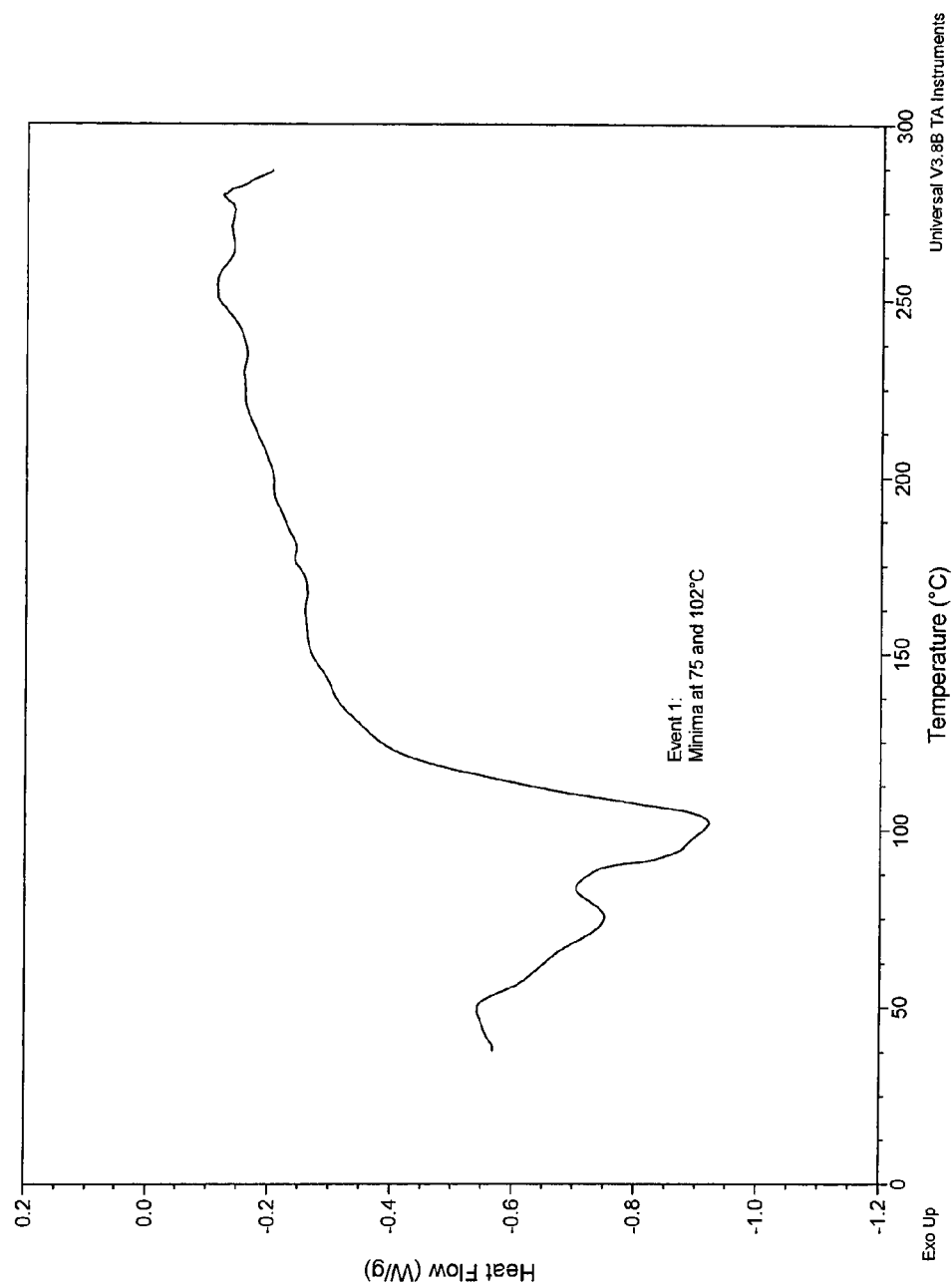
FIG. 13 is a differential scanning calorimetry (DCS) thermogram of the hydrochloride salt of (S)-3-aminomethyl-7-(3-hydroxy-propoxy)-3H-benzo[c][1,2]oxaborol-1-ol referred to as polymorph form HCl3.

DSC thermogram was acquired using a TA Instruments Q100 Differential Scanning calorimeter. A sample of (S)-3-aminomethyl-7-(3-hydroxy-propoxy)-3H-benzo[c][1,2]oxaborol-1-ol polymorph form HCl3 prepared as described above was accurately weighed out directly into an aluminum DSC pan. The pan was sealed by applying pressure by hand and pushing each part the pan together (also known as a loose lid configuration). The temperature was ramped at a rate of 15° C./minute. A broad endothermic transition exhibiting minima at 75 and 102° C. was measured. The DSC thermogram is shown in FIG. 13.

Figure 14:
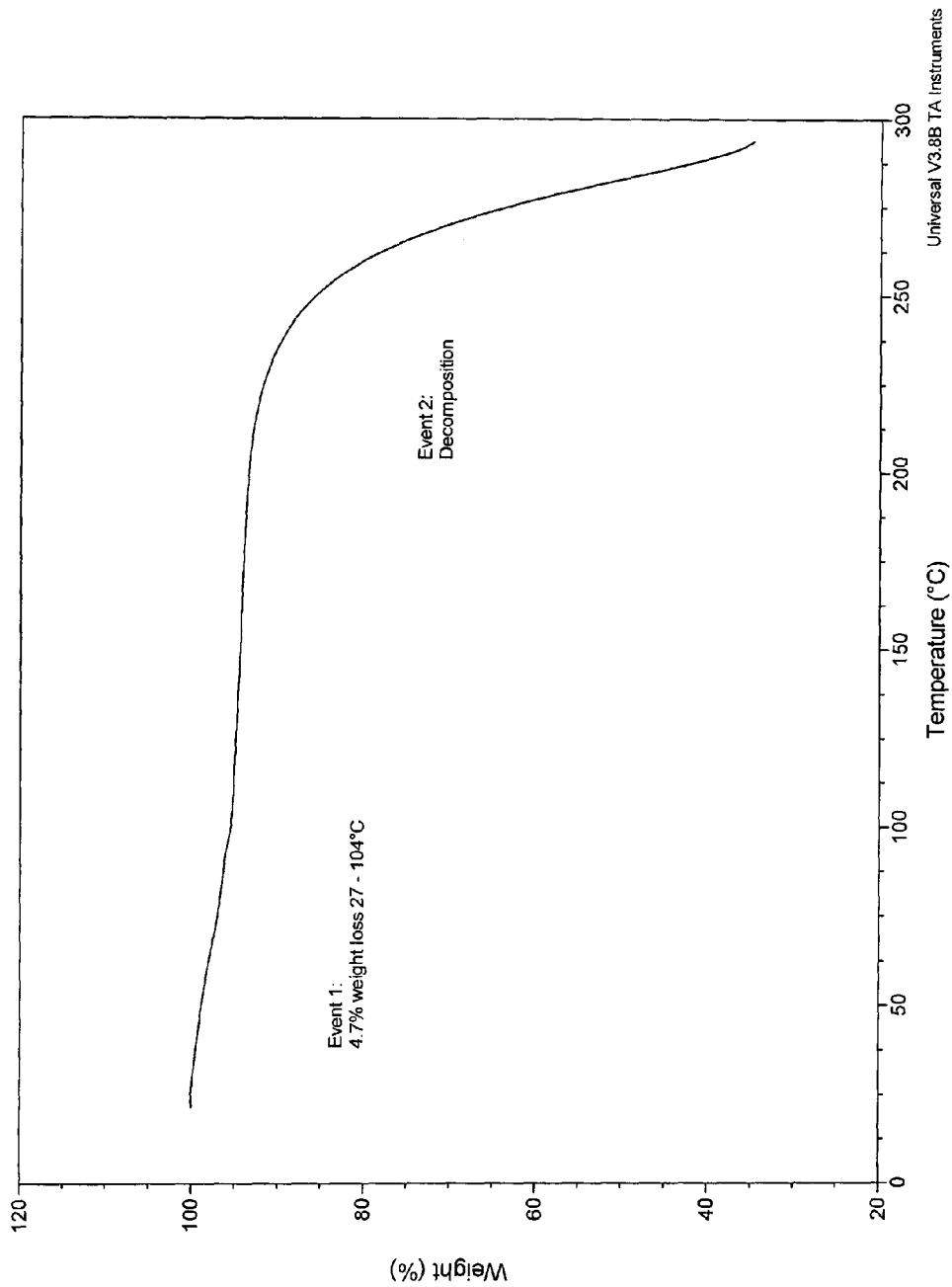
FIG. 14 is a thermogravimetric analyzer (TGA) thermogram of the hydrochloride salt of (S)-3-aminomethyl-7-(3-hydroxy-propoxy)-3H-benzo[c][1,2]oxaborol-1-ol referred to as polymorph form HCl3.

The TGA thermogram of polymorph form HCl3 was acquired using a TA Instruments Q500 Thermogravimetric Analyzer. The sample pan was tared, and sample of (S)-3-aminomethyl-7-(3-hydroxy-propoxy)-3H-benzo[c][1,2]oxaborol-1-ol polymorph form HCl3 prepared as described above was placed in the pan. The temperature was ramped at a rate of 15° C./minute. A weight-loss of 4.7% between 27 and 104° C. was observed and is associated with water-loss due to dehydration. Further decomposition is observed beyond 214° C. The TGA thermogram is shown in FIG. 14.

Figure 15:
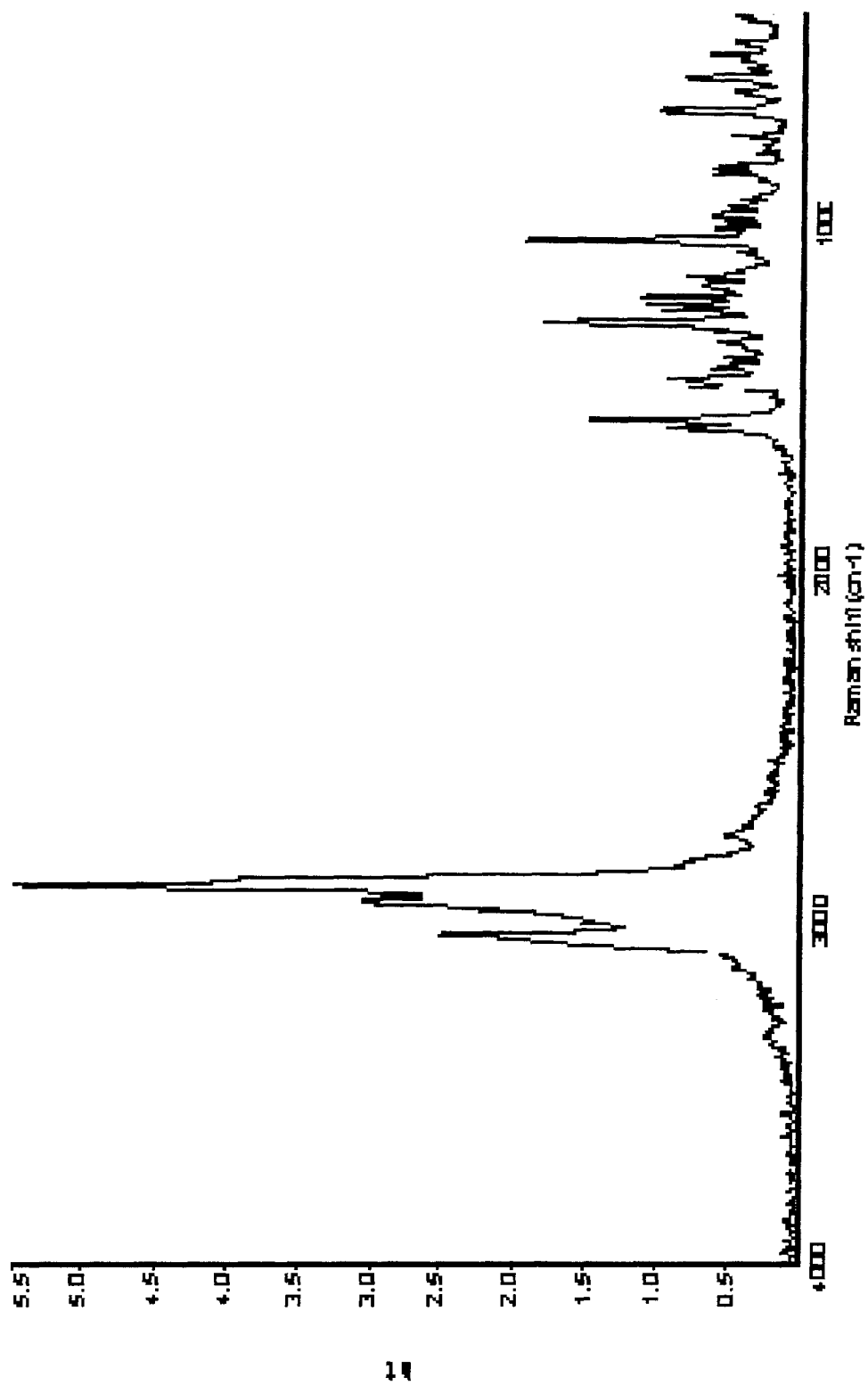
FIG. 15 is a Raman spectroscopy analysis of the hydrochloride salt of (S)-3-aminomethyl-7-(3-hydroxy-propoxy)-3H-benzo[c][1,2]oxaborol-1-ol referred to as polymorph form HCl2.
Figure 16A:
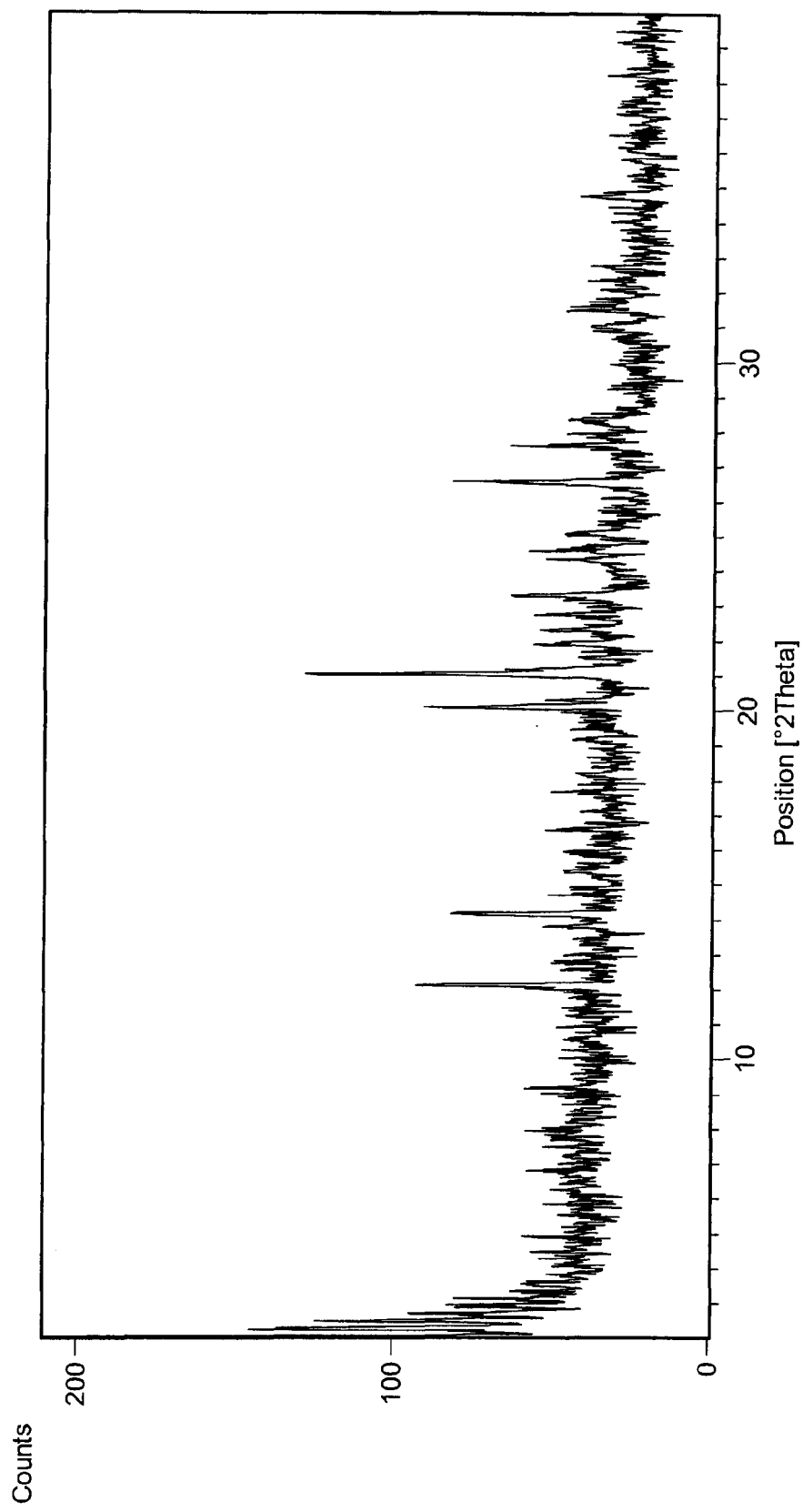
FIG. 16A is a second X-ray powder diffraction (XRPD) pattern of the hydrochloride salt of (S)-3-aminomethyl-7-(3-hydroxy-propoxy)-3H-benzo[c][1,2]oxaborol-1-ol referred to as polymorph form HCl2.

Form HCl2
Method of Preparation:
A solution of 2-butanone (10 mL) was saturated with Form HCl4. The saturated solution was transferred into a 20 mL scintillation vial and the contents were allowed to evaporate under ambient conditions in a laboratory hood. Evaporation resulted in the formation of trace quantities of a white precipitate in the presence of an oil. The white precipitate was isolated by vacuum filtration and exhibited a pXRD pattern consistent with Form HCl2. FIG. 15 shows a FT-Raman spectrum recorded on a Nicolet NXR 9650 FT-Raman Spectrometer at a resolution of 4 cm$^{-1}$ with excitation from a Nd:YVO4 laser ($\lambda$=1064 nm). Form HCl2 exhibits peaks at the following wavenumbers (cm$^{-1}$): 3051.4, 2954.9, 2941.2, 2910.4, 1604.2, 1580.8, 1453.3, 1297.9, 1262.8, 1247.3, 1226.8, 1167.6, 1068.4, 686.7, 597.2. In exemplary embodiments, the entire list of peaks, or a subset thereof, may be sufficient to characterize (S)-3-aminomethyl-7-(3-hydroxy-propoxy)-3H-benzo[c][1,2]oxaborol-1-ol polymorph form HCl2. FIG. 16A show an X-ray powder diffraction pattern of (S)-3-aminomethyl-7-(3-hydroxy-propoxy)-3H-benzo[c][1,2]oxaborol-1-ol polymorph form HCl2 prepared as described above, acquired using a PANalytical X'Pert Pro diffractometer. Samples were gently flattened onto a zero-background silicon insert sample holder. A continuous 2θ scan range of 2 to 40 degrees was used with a CuKα radiation source and a generator power of 40 kV and 45 mA. A 2θ step size of 0.017 degrees/step with a step time of 20.0 seconds was used. Samples were rotated at 30 rpm. Experiments were performed at room temperature and at ambient humidity. FIG. 16B lists peaks at degrees 2θ±0.2 degrees 2θ and d-spacing values which characterize Form HCl2 as shown in FIG. 16A. In exemplary embodiments, the entire list of peaks, or a subset thereof, may be sufficient to characterize (S)-3-aminomethyl-7-(3-hydroxy-propoxy)-3H-benzo[c][1,2]oxaborol-1-ol polymorph form HCl2.

Figure 17:
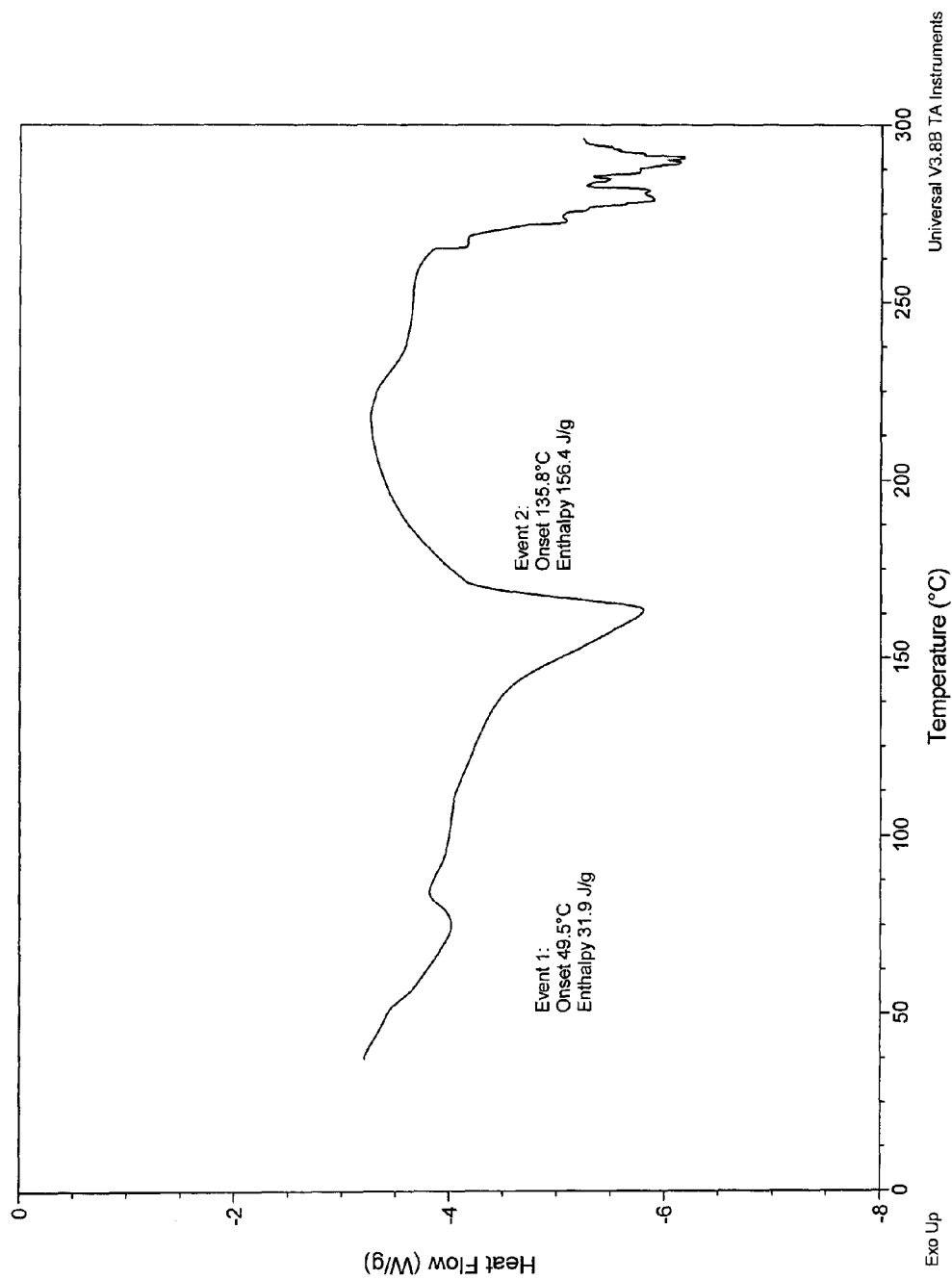
FIG. 17 is a DSC thermogram of the hydrochloride salt of (S)-3-aminomethyl-7-(3-hydroxy-propoxy)-3H-benzo[c][1,2]oxaborol-1-ol referred to as polymorph form HCl2.

FIG. 17 shows a DSC thermogram acquired using a TA Instruments Q100 Differential Scanning calorimeter. A sample of (S)-3-aminomethyl-7-(3-hydroxy-propoxy)-3H-benzo[c][1,2]oxaborol-1-ol polymorph form HCl2 prepared as described above was accurately weighed out directly into an aluminum DSC pan. The pan was sealed by applying pressure by hand and pushing each part the pan together (also known as a loose lid configuration). The temperature was ramped at a rate of 15° C./minute. An endothermic transition having an onset of 49.5° C. and an enthalpy of 31.9 J/g was measured. An additional endotherm having an onset of 135.8° C. and an enthalpy of 156.4 J/g was measured.

Form HCl5
Form HCl5 is unstable when stored at room temperature and converts to Form HCl3.
Method of Preparation:
A solution of isopropanol containing 10% water by volume was added to a vial containing approximately 25 mg of (S)-3-aminomethyl-7-(3-hydroxy-propoxy)-3H-benzo[c][1,2] oxaborol-1-ol polymorph form HCl4. The resulting mixture was stirred as the temperature was cycled between 0 and 40° C. over the course of 48 hours. The solution was isolated by filtration and evaporated to dryness. The freshly isolated product was verified to be a new crystalline form (Form HCl5).

Figure 18:
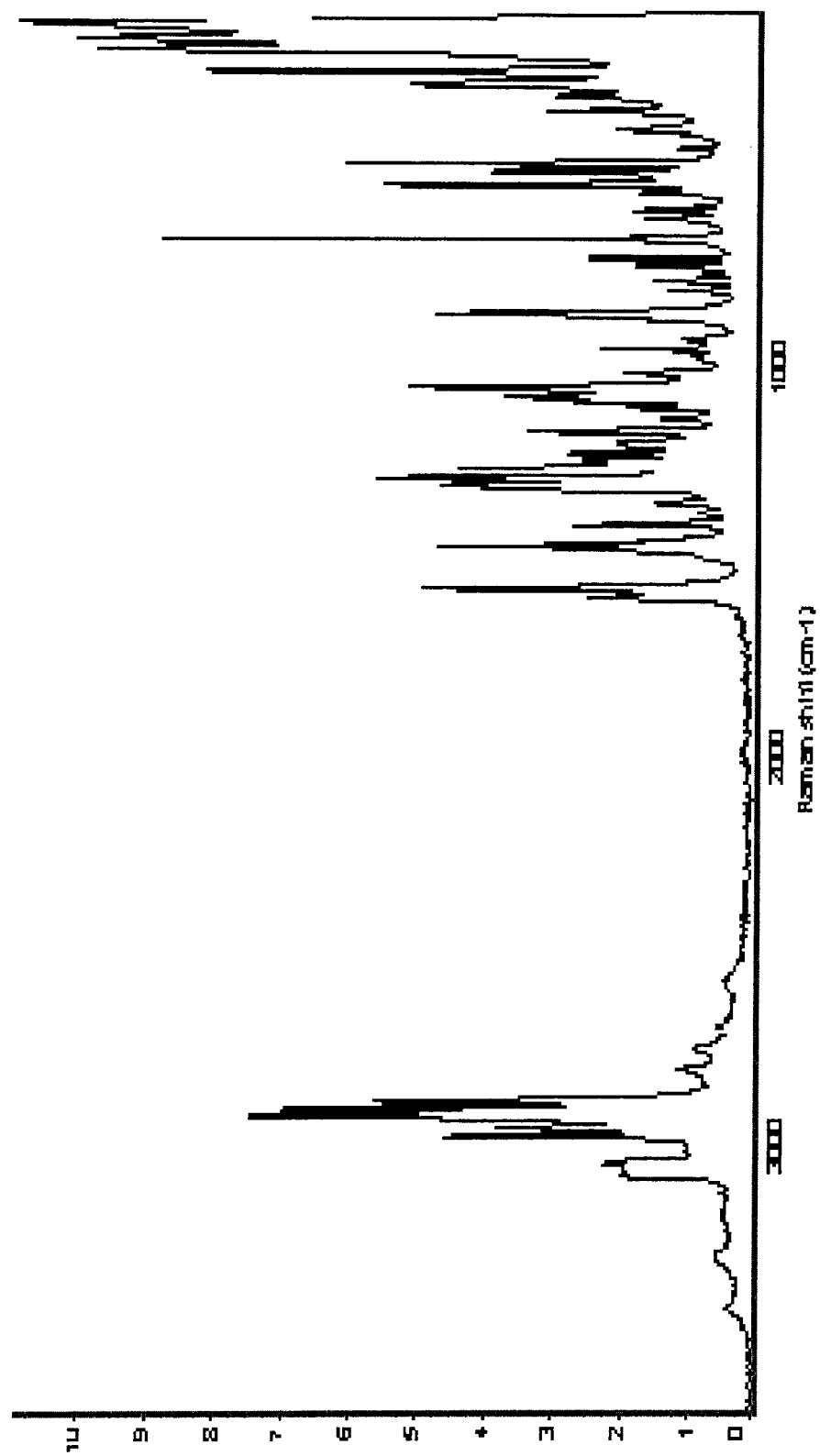
FIG. 18 is a Fourier transform Infrared (FT-IR) spectroscopy analysis of a new polymorph of the hydrochloride salt of (S)-3-aminomethyl-7-(3-hydroxy-propoxy)-3H-benzo[c][1,2]oxaborol-1-ol referred to as polymorph form HCl5.

FIG. 18 shows a FT-Raman spectrum of polymorph form HCl5 recorded on a Nicolet NXR 9650 FT-Raman Spectrometer at a resolution of 4 cm$^{-1}$ with excitation from a Nd:YVO4 laser ($\lambda$=1064 nm). Form HCl5 exhibits peaks at the following wavenumbers (cm$^{-1}$): 2931.0, 2917.7, 2896.2, 1583.8, 1474.0, 1302.6, 1062.0, 685.6, 546.4, 493.3, 294.0, 262.2, 206.8, 180.9, 140.4. In exemplary embodiments, the entire list of peaks, or a subset thereof, may be sufficient to characterize (S)-3-aminomethyl-7-(3-hydroxy-propoxy)-3H-benzo[c][1,2]oxaborol-1-ol polymorph form HCl5.

It is to be understood that the present invention covers all combinations of aspects with all other suitable aspects and/or exemplary embodiments described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A crystalline polymorph of a hydrochloride salt of (S)-3-aminomethyl-7-(3-hydroxy-propoxy)-3H-benzo[c][1,2]oxaborol-1-ol characterized by having essentially all of the °2θ values listed in Table 1±0.2°2θ:

TABLE 1

| Pos. [°2θ] | d-spacing [Å] |
|---|---|
| 12.1 | 7.3 |
| 14.2 | 6.2 |
| 18.2 | 4.9 |
| 19.2 | 4.6 |
| 20.1 | 4.4 |
| 21.0 | 4.2 |
| 21.9 | 4.1 |
| 22.7 | 3.9 |
| 24.3 | 3.7 |
| 26.6 | 3.4 |
| 27.6 | 3.2 |
| 30.9 | 2.9 |
| 31.5 | 2.8 |
| 34.7 | 2.6 |
| 39.5 | 2.3. |

2. A crystalline polymorph of a hydrochloride salt of (S)-3-aminomethyl-7-(3-hydroxy-propoxy)-3H-benzo[c][1,2]oxaborol-1-ol having, upon X-ray crystallographic analysis, crystal parameters of substantially the following values:
  Crystallographic system: orthorhombic
  Space group: $P2_12_12_1$
  Crystal dimensions: a=9.1045(2) Å, b=10.3107(2) Å, c=14.5988(3) Å
  α=90.00°, β=90.00°, γ=90.00°
  Volume 1370.44(5) Å$^3$
  Z, calculated density 4, 1.326 g cm$^{-3}$.

3. A crystalline polymorph of a hydrochloride salt of (S)-3-aminomethyl-7-(3-hydroxy-propoxy)-3H-benzo[c][1,2]oxaborol-1-ol, characterized by having upon Raman spectroscopic analysis, all of the peaks having substantially the wavenumbers (cm$^{-1}$) of 3076.4, 3054.6, 2987.4, 2975.5, 2954.2, 2928.0, 2909.8, 2896.0, 1578.6, 1298.2, 1291.6, 1263.0, 1226.8, 1068.9, and 694.9, ±50 wave numbers.

4. The crystalline polymorph of claim 3, having a multiplet of peaks between about 2800 and about 3200 cm$^{-1}$, ±50 wavenumbers, and another multiplet of peaks between about 1600 and about 600 cm$^{-1}$, ±50 wavenumbers, and an essential absence of peaks between about 1800 and about 2200 cm$^{-1}$, ±50 wavenumbers.

5. A pharmaceutical composition comprising:
  a) the crystalline polymorph of claim 1; and
  b) at least one excipient or carrier.

6. A method for treating a disease in an animal suffering from a disease, comprising:
  administering to the animal a therapeutically effective amount of the crystalline polymorph of claim 1,
  wherein said disease is associated with a bacteria.

7. The method of claim 6, wherein the bacteria is a Gram negative bacteria.

8. The method of claim 6, wherein the bacteria is selected from the group consisting of *Neisseria* species, *Escherichia* species, *Shigella* species, *Salmonella* species, *Yersinia* species, *Klebsiella* species, *Proteus* species, *Enterobacter* species, *Serratia* species, *Vibrio* species, *Campylobacter* species, *Helicobacter* species, *Pseudomonas* species, *Bacteroides* species, *Haemophilus* species, *Bordetella* species, *Legionella* species, *Francisella* species, *Brucella* species, *Pasteurella* species, *Gardnerella* species, *Spirochetes* species, *Chlamydia* species and *Rickettsiae* species.

9. The method of claim 6, wherein the disease is selected from the group consisting of meningitis, gonorrhea, otitis, otitis extema, folliculitis, diarrhea, urinary tract infections, sepsis, HAP, bacteremia, endocarditis, gastroenteritis, Typhoid fever, supsis, endocarditis, sinusitis, bubonic plague, enteric fever, hospital-acquired infection, skin and skin-structure infection, pneumonia, cholera, chronic gastritis, osteomylitis, burn-wound infections, corneal infections, periodontal disease, aspriation pneumonia, piglottitis, septic arthritis, chancroid, vaginitis, whooping cough, pontiac fever, tularemia, brucellosis, syphilis, Lyme disease, chlamydia, Rocky Mountain spotted fever, typhus, tracheobronchitis, walking pneumonia, urethritis, pyelonenephritis, intra-abdominal infection, febrile neutropenia, pelvic infection, bacteraemia, and septicaemia.

10. The method of claim 6, wherein the disease is pneumonia.

11. A crystalline polymorph of (S)-3-aminomethyl-7-(3-hydroxy-propoxy)-3H-benzo[c][1,2]oxaborol-1-ol.HCl having, upon X-ray crystallographic analysis, essentially all of the following °2θ values, ±0.2°2θ: 7.8, 12.3, 14.0, 20.2, 21.3, 22.4, 23.3, 24.7, 27.6, and 32.1.

12. A crystalline polymorph of (S)-3-aminomethyl-7-(3-hydroxy-propoxy)-3H-benzo[c][1,2]oxaborol-1-ol.HCl having, upon X-ray crystallographic analysis, essentially all of the following °2θ values, ±0.2°2θ: 6.2, 8.8, 9.8, 12.4, 13.9, 17.7, 22.3, 23.1, 24.3, 24.8, 26.1, 27.2, 28.0, 30.9, 32.2, and 33.

13. A crystalline polymorph of a hydrochloride salt of (S)-3-aminomethyl-7-(3-hydroxy-propoxy)-3H-benzo[c][1,2]oxaborol-1-ol, produced by evaporation and/or recrystallization from a solution of (S)-3-aminomethyl-7-(3-hydroxy-propoxy)-3H-benzo[c][1,2]oxaborol-1-ol.HCl wherein the concentration of (S)-3-aminomethyl-7-(3-hydroxy-propoxy)-3H-benzo[c][1,2]oxaborol-1-ol.HCl is from about 11 mg/mL to about 30 mg/mL.

14. A crystalline polymorph of a hydrochloride salt of (S)-3-aminomethyl-7-(3-hydroxy-propoxy)-3H-benzo[c][1,2]oxaborol-1-ol, produced by evaporation and/or recrystallization from a solution of (S)-3-aminomethyl-7-(3-hydroxy-propoxy)-3H-benzo[c][1,2]oxaborol-1-ol.HCl wherein the concentration of (S)-3-aminomethyl-7-(3-hydroxy-propoxy)-3H-benzo[c][1,2]oxaborol-1-ol.HCl is from about 15 mg/mL to about 50 mg/mL.

* * * * *